(12) United States Patent
Yuds et al.

(10) Patent No.: US 12,102,790 B2
(45) Date of Patent: Oct. 1, 2024

(54) CONNECTED DRUG DELIVERY SYSTEM FOR ERYTHROPOIETIN STIMULATING AGENTS

(71) Applicant: Fresenius Medical Care Holdings, Inc., Waltham, MA (US)

(72) Inventors: David Yuds, Antioch, CA (US); Sameer Peesapati, Toronto (CA)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 980 days.

(21) Appl. No.: 17/028,366

(22) Filed: Sep. 22, 2020

(65) Prior Publication Data

US 2021/0187189 A1 Jun. 24, 2021

Related U.S. Application Data

(60) Provisional application No. 62/952,828, filed on Dec. 23, 2019.

(51) Int. Cl.
*A61M 5/142* (2006.01)
*A61M 5/172* (2006.01)
*G16H 20/17* (2018.01)

(52) U.S. Cl.
CPC ...... *A61M 5/14248* (2013.01); *A61M 5/1723* (2013.01); *G16H 20/17* (2018.01); *A61M 2005/14208* (2013.01); *A61M 2005/14252* (2013.01); *A61M 2005/1726* (2013.01); *A61M 2202/0433* (2013.01); *A61M 2205/3327* (2013.01); *A61M 2205/3553* (2013.01); *A61M 2205/52* (2013.01); *A61M 2230/04* (2013.01)

(58) Field of Classification Search
None
See application file for complete search history.

(56) References Cited

U.S. PATENT DOCUMENTS

| 8,348,922 | B2 | 1/2013 | Imran |
| 8,536,123 | B2 | 9/2013 | Cho |
| 9,616,107 | B2 | 4/2017 | VanAntwerp et al. |
| 10,319,478 | B2 | 6/2019 | Fuertinger et al. |
| 2003/0065294 | A1* | 4/2003 | Pickup ................ B41J 2/16505 |
| | | | 604/304 |

(Continued)

FOREIGN PATENT DOCUMENTS

| WO | 2009/079589 A2 | 6/2009 |
| WO | 2015/187802 A1 | 12/2015 |

OTHER PUBLICATIONS

Joseph, Bellal., et al. "Non-invasive hemoglobin monitoring," International Journal of Surgery; vol. 33, Part B, Sep. 2016, pp. 254-257.

(Continued)

*Primary Examiner* — Manuel A Mendez
(74) *Attorney, Agent, or Firm* — Kilyk & Bowersox, P.L.L.C.

(57) ABSTRACT

Methods to treat anemia are provided whereby an erythropoietin stimulating agent (ESA) and an iron supplement are administered by a wearable device, based on patient parameters sensed by the wearable device. The method can involve monitoring patient parameters and dosing an ESA and an iron supplement in real-time, via the wearable device.

19 Claims, 25 Drawing Sheets

(56) References Cited

U.S. PATENT DOCUMENTS

| | | | |
|---|---|---|---|
| 2004/0202554 A1 | 10/2004 | Takeuchi et al. | |
| 2004/0267240 A1* | 12/2004 | Gross | A61B 1/041 604/20 |
| 2005/0277912 A1* | 12/2005 | John | A61M 5/16827 604/890.1 |
| 2006/0031099 A1* | 2/2006 | Vitello | G16H 20/17 604/82 |
| 2008/0033402 A1* | 2/2008 | Blomquist | G16H 20/13 604/890.1 |
| 2008/0050749 A1 | 2/2008 | Amann-Zalan et al. | |
| 2010/0130910 A1* | 5/2010 | Berenson | A61K 9/703 604/20 |
| 2010/0292632 A1 | 11/2010 | Mulvihill et al. | |
| 2013/0052136 A1 | 2/2013 | Chamney et al. | |
| 2014/0074062 A1 | 3/2014 | Caffey et al. | |
| 2014/0142508 A1 | 5/2014 | Dilanni et al. | |
| 2016/0045158 A1* | 2/2016 | Hsu | A61B 5/14532 600/347 |
| 2017/0056585 A1 | 3/2017 | Kamen et al. | |
| 2017/0128532 A1 | 5/2017 | Rodriguez et al. | |
| 2017/0157329 A1 | 6/2017 | Richter et al. | |
| 2018/0125419 A1* | 5/2018 | Yun | A61B 5/4836 |
| 2018/0217166 A1 | 8/2018 | Gonzalez et al. | |
| 2019/0013090 A1 | 1/2019 | Chait et al. | |
| 2019/0015581 A1 | 1/2019 | Searle et al. | |
| 2019/0091457 A1 | 3/2019 | Wagstaff | |
| 2019/0214967 A1 | 7/2019 | Shor et al. | |
| 2019/0254541 A1 | 8/2019 | Di Achille et al. | |
| 2019/0269862 A1 | 9/2019 | Gray | |

OTHER PUBLICATIONS

Labios, Liezel "Wearable Ultrasound Patch Monitors Blood Pressure Deep Inside Body," UC San Diego News Center, Sep. 12, 2018, 4 pages.

Irving, Michael, "'Twist fridges' could cool down by unraveling fibers," ISO 18562, VOC and Particle Testing, Materials, University of Texas at Dallas, New Atlas, Oct. 14, 2019, 4 pages.

SUNON® "Ultra Micro Cooling Device" Product Brochure, 2013.

Sophie Seronie-Vivien, "Epoetin Alfa and Intravenous Iron Sucrose to Treat Severe Anemia in a Patient with Chronic Radiation Enteropathy", Medical Oncology, vol. 20, No. 3, pp. 301-306, 2003.

International Search Report and Written Opinion dated Jan. 13, 2021, including Notification of Transmittal (Form PCT/ISA/220) for related International Application No. PCT/US2020/051060, 15 pages total.

\* cited by examiner

CONNECTED DRUG DELIVERY SYSTEM FOR ERYTHROPOIETIN STIMULATING AGENTS

CROSS-REFERENCE TO RELATED APPLICATION

The present application claims priority under 35 U.S.C. § 119 from U.S. Provisional Application No. 62/952,828 filed Dec. 23, 2019, the disclosure of which is expressly incorporated herein by reference in its entirety.

FIELD OF THE INVENTION

The present invention relates to a device, system, and method for automatically administering drugs and supplements to a patient. The present invention also relates to a device, system, and method for treating anemia.

BACKGROUND OF THE INVENTION

When the human body experiences reduced oxygen levels at higher elevations, it begins to produce more hemoglobin (Hgb) in the blood to improve the distribution of the available oxygen. Dialysis patients similarly suffer from a lack of enough hemoglobin, called anemia (a deficiency in red blood cells) because the kidneys cannot produce hormones necessary to signal bone marrow to produce more hemoglobin. Anemia especially causes fatigue in dialysis patients because the patient's organs are not getting enough oxygen to function properly.

Continuous intra- and inter-dialytic monitoring is critical for patients with Chronic Kidney Disease (CKD) and End Stage Renal Disease (ESRD). Blood pressure regulation is important for kidney disease patients and this involves regulation of renin-angiotensin and erythropoietin hormones. With ESRD these functions are compromised.

Chemotherapy attacks rapidly dividing cells, including the cells that eventually form red blood cells. Therefore, cancer patients on chemotherapy need more erythropoietin hormones to stimulate the production of more hemoglobin.

Epoetin alfa is a human erythropoietin produced in cell culture using recombinant DNA technology and is used to treat anemia. This medication is very similar to the natural substance in your body (erythropoietin) that prevents anemia. It works by signaling the bone marrow to make more red blood cells and is paired with iron supplements. Iron is an important component of hemoglobin, the substance in red blood cells that carries oxygen from your lungs to transport it throughout the body. Hemodialysis patients can receive iron intravenously in the form of VENOFER, an iron supplement available from American Regent, Inc., of Shirley, New York. Hemoglobin represents about two-thirds of the body's iron. Without enough iron, the body cannot make enough healthy oxygen-carrying red blood cells. Without healthy red blood cells, the body cannot get enough oxygen.

Epoetin is manufactured and marketed by Amgen, of Thousand Oaks, California, under the tradename EPOGEN. The average cost per patient in the U.S. was $8,447 in 2009 and is steadily increasing every year. For several years, epoetin alfa has accounted for the single greatest drug expenditure paid by the U.S. Medicare system.

VENOFER is currently available as a brand name drug only; a generic version is not yet available.

Because drugs useful for anemia management, such as EPOGEN and VENOFER, are so expensive, the costs consume a significant portion of the costs reimbursed by Medicare for hemodialysis treatments, which limits funds available for improved quality of care and the development of innovative, next generation dialysis devices.

Furthermore, EPOGEN is administered in regular, prescribed doses without regard to a patient's daily red blood cell count. A hemoglobin concentration of less than 10 g/dL is advised before using EPOGEN and the dosage is based on the patient's medical condition, weight, and response to treatment. Costly blood tests must therefore be done often to check how well the medication is working and to decide the correct dose. There is also great complexity in administering the drug.

Epoetin alfa may sometimes cause or worsen high blood pressure, especially in patients with long-term kidney failure. This effect may be caused by the number of red blood cells increasing too quickly, usually within the first three months of starting treatment. Therefore, it is particularly important to not overdose the patient. With EPOGEN treatments, hemoglobin levels usually increase starting in two to six weeks and the patient's blood needs to be tested regularly to make sure the EPOGEN is working. It is recommended to test the blood at least weekly at the beginning. Other drug alternatives like ARANSEP (Darbepoetin alfa), available from Amgen, Thousand Oaks, California, and MIRCERA (Epoetin beta), available from F. Hoffmann-La Roche AG, Basel, Switzerland, are also costly and have different dosing requirements and reaction times that complicate switching between drugs, as shown in the table below:

TABLE 1

Mircera Starting Doses for Adult Patients Currently Receiving an ESA

| Previous Weekly Epoetin alfa Dose (units/week) | Previous Weekly Darbepoetin alfa Dose (mcg/week) | Mircera Dose | |
|---|---|---|---|
| | | Once Monthly (mcg/month) | Once Every Two Weeks (mcg/every two weeks) |
| less than 8000 | less than 40 | 120 | 60 |
| 8000 to 16000 | 40 to 80 | 200 | 100 |
| More than 16000 | more than 80 | 360 | 180 |

VENOFER also requires careful calculation in dosing. For example, instructions are to administer VENOFER at a dose of 0.5 mg/kg, not to exceed 100 mg per dose, every four weeks for 12 weeks given undiluted by slow intravenous injection over 5 minutes or diluted in 25 mL of 0.9% NaCl and administered over 5 to 60 minutes.

These dosing calculations, testing, and the time spent administering them increases labor costs and is compounded by, in some cases, more than 30 hemodialysis patients in a clinic. Peritoneal dialysis (PD) patients also need these drugs and testing for efficacy.

The amount of time required for patients to be tested, treated, and retested is burdensome, especially when factoring in travel and the number of touchpoints. Touchpoints can include patient to dialysis technician to lab technician to nephrologist to patient to pharmacist to dialysis technician to patient, all for one cycle of treatment.

FIG. 1 shows the current state of treatments for anemia using prescribed ESAs. As can be seen in FIG. 1, a patient goes to a doctor or a lab to receive a blood check-up per the patient's care plan. Blood drawn from the patient is sent to a laboratory for blood testing. The results of the blood testing are then dispatched to the patient's attending physician. The attending physician reviews the blood test results and, if needed, an ESA is prescribed by the attending physician. The prescription is then filled and administered to the patient. Many touchpoints are involved.

Current methods of administration rely on blood testing done once every two to four weeks, depending on the disease group and an ESA prescription being issued based on hemoglobin (Hgb) levels. It takes the body nearly two to three weeks for ESA to take effect and show considerable improvements, although currently this can only be realized with subsequent blood tests.

There is a need to provide adaptive dosing for improved quality of life.

SUMMARY OF THE INVENTION

The present invention provides automated anemia management in patients suffering from chronic kidney disease or other chronic ailments that cause erythropoietin deficiencies.

The present invention also provides reduced costs for a hemodialysis or peritoneal dialysis treatment through automated delivery of erythropoietin and an iron supplement.

According to various embodiments, blood oxygenation, partial $O_2$ saturation, Hematocrit, Hemoglobin, and blood pressure measurements, are measured and values are used to predict the need for ESA hormones for anemia and blood pressure regulation in patients.

The present invention addresses the problem of anemia management for CKD, cancer, and other disease groups where ESAs can be prescribed long-term.

The present invention provides an erythropoietin delivery system that interfaces with a prescribed patch and wirelessly connects to the patient's nephrologist. In some embodiments, the delivery system can also deliver an iron supplement. The device can be wearable and can continuously monitor a patient's blood oxygenation, partial $O_2$ saturation, hematocrit, and hemoglobin. The wearable device can have a built-in blood pressure monitor or can wirelessly connect, for example, by Bluetooth, to a blood pressure cuff so that blood pressure measurements can be integrated into a nephrologist's report. The blood pressure measurements can be measured directly by the wearable device, for example, by using ultrasonic sensors or piezoelectric sensors. An exemplary system is shown at https://ucsdnews.ucsd.edu/press-release/wearable_ultrasound_patch_monitors_blood_pressure_deep_inside_body.

Accordingly, to various embodiments, a nephrologist can upload a new prescription and the device integrates control to administer one or more drugs, for example, an ESA such as EPOGEN, and an iron supplement such as VENOFER. The control can be based on the prescription data, patient parameters, or both. The device can eliminate the need for clinic staff to draw blood, test it, perform their own dosing calculations, and manually administer the drugs with syringes. Not only does this result in a time-savings, but it also uses the drugs, for example, VENOFER and EPOGEN, more efficiently such that none of it goes to waste. A live data stream can be used to show whether hemoglobin and oxygen saturation are adequate. A built-in blood pressure monitor or a paired blood pressure cuff can be used to evaluate the needs of the patient.

The wearable device can synchronize with a receiving device, for example, an Apple or Samsung smartwatch, a cellphone, a laptop, a physician network, a pharmacy network, or the like. Such a receiving device can be used to monitor the patient, resulting in less interference with the patient's daily life. The present invention can also be used to treat other symptoms of anemia caused by treatments such as cancer chemotherapy, conditions like hypothyroidism, iron deficiencies, and the like. By utilizing measured quantities or other values, such as the combined hematocrit and oxygen saturation levels, in the data stream, drugs such as EPOGEN and VENOFER can be more accurately administered.

In exemplary embodiments, a system is provided that monitors closely for changes in the Hgb levels through $SpO_2$ measurements. Based on such changes, the wearable device is able to determine a required treatment to maintain a steady Hgb level of from 13 to 15 g/dL. The treatment can involve administering one or more drugs, for example, both an ESA and an iron supplement.

BRIEF DESCRIPTION OF THE DRAWINGS

The invention may be more fully understood with reference to the accompanying drawings. The drawings are intended to illustrate, not limit, the present teachings.

DETAILED DESCRIPTION OF THE INVENTION

Figure 1:
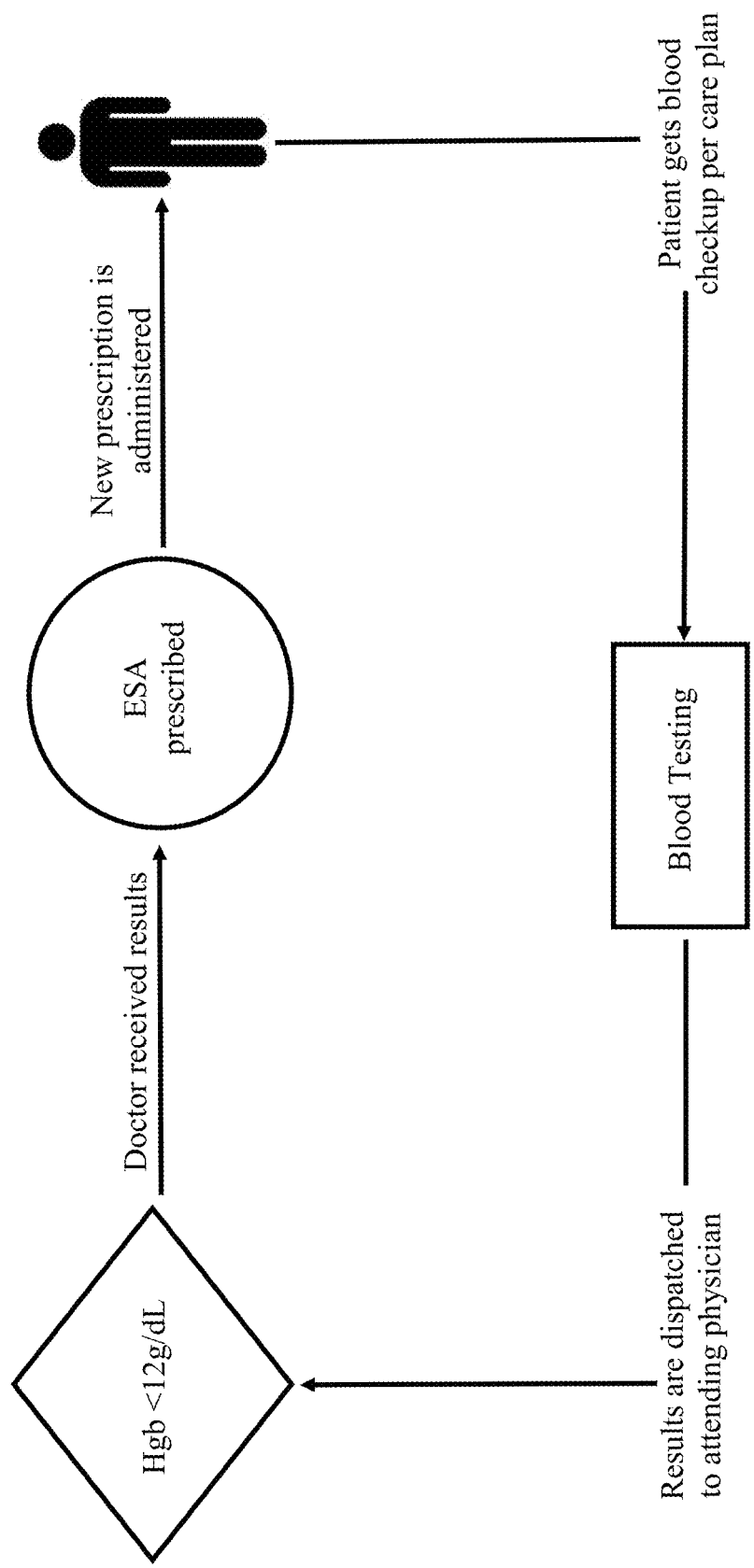
FIG. 1 is a schematic illustration of a currently available method of prescribing and administering an erythropoietin stimulating agent (ESA).

According to one or more embodiments of the present invention, a wearable device is provided that comprises a housing configured to be attached to the skin of a patient during use. The wearable device comprises an injector assembly at least partially housed in the housing. The injector assembly is configured to inject a first drug into the patient, through the patient's skin. The injector assembly can also be configured to inject a second drug into the patient, also through the patient's skin. By "inject," what is meant is injection via a needle, syringe, cannula, microneedle, microneedle array, or via a transdermal device. In some cases, the first drug can be injected via a syringe whereas the second drug can be injected by a transdermal patch.

The wearable device can also include a first sensing system configured to sense one or more patient parameters that are indicative of a need to administer the first drug to the patient. The first sensing system can comprise one or more sensors and a control signal generator. The control signal generator can be configured to generate a control signal in response to one or more of the patient parameters that are sensed.

The wearable device can also include a control system within the housing. The control system can be configured to receive a control signal from the first sensing system. The control system can activate the injector assembly based on a control signal received, for example, to inject the first drug into the patient. The control system can further be configured to activate the injector assembly to inject the second drug into the patient, for example, based on a second control signal received.

In addition to the first sensing system, a second sensing system can be provided that is configured to sense one or more patent parameters that are indicative of a need to administer the second drug to the patient. The second sensing system can comprise one or more second sensors and a second control signal generator. The second control signal generator can be configured to generate a second control signal in response to the one or more patient parameters that are sensed by the second sensing system. The control system can further be configured to receive a second control signal from the second sensing system. Based on the second control signal received, the control system can activate the injector assembly to inject the second drug into the patient.

The wearable device can comprise a first reservoir within the housing, for example, containing a supply of the first drug. The wearable device can comprise a second reservoir within the housing, for example, containing a supply of the second drug. Each of the first reservoir and the second reservoir can independently be in fluid communication with the injector assembly. The first drug and the second drug can be interdependent on one another. In an exemplary device, the first drug can be an erythropoietin and the second drug can be an iron supplement. The wearable device can be configured to treat and control anemia in a patient. The first drug can be epoetin alfa, epoetin beta, darbepoetin alfa or a combination thereof. The second drug can be an iron supplement supplied from the second reservoir or supplied from a transdermal patch.

The control system can be configured to receive an input signal from a remote device, for example, from a cell phone, a tablet, a computer, a smartwatch, a smartphone, a smart speaker, or the like. The input signal can comprise a set of instructions for the control system to carry out. The set of instructions can comprise a timing instruction and an amount instruction, to be used by the control system, to activate the injector assembly. The set of instructions received from the remote device can be used along with the control signal from the first sensing system, the control signal from the second sensing system, or both, to activate the injector assembly. The set of instructions and one or more control signals can be used to control the timing and amount of injection of the first drug into the patient, and the timing and amount of injection of the second drug into the patient, or both.

A system is also provided according to the present invention and includes a wearable device as described herein and a remote device. The remote device can comprise a sensor configured to sense a patient parameter. The remote device can also comprise a signal generator configured to generate a remote-control signal indicative of the sensed patient parameter. The control system can be configured to receive the remote-control signal from the remote device, and, based on the received remote control signal and the control signal received from the first sensing system, activate the injector assembly. The activation of the injector assembly can be controlled so as to control the timing and amount of injection of the first drug into the patient and the timing and amount of injection of the second drug into the patient. The remote device can comprise, for example, a pulse oximeter, a blood pressure sensor, a heartbeat rate sensor, or a combination thereof.

The first sensing system of the wearable device can comprise a pulse oximeter, a hematocrit sensor, a hemoglobin sensor, a blood pressure sensor, or a combination thereof. If a pulse oximeter is included in the first sensing system, it can comprise a non-invasive blood oxygen saturation sensor. If a blood pressure sensor is included in the first sensing system, it can comprise a non-invasive blood pressure sensor. The first sensing system can comprise a blood pressure sensor that comprises a cuff, a piezoelectric transducer, or an array of piezoelectric transducers.

The injector assembly can comprise a first injector device configured to inject the first drug into the patient through the patient's skin, and a second injector device configured to inject the second drug into the patient through the patient's skin. In some embodiments, the injector assembly can comprise a single injector device configured to inject the first drug and the second drug simultaneously, alternately, or intermittently, into the patient through the patient's skin. The injector assembly can comprise a retractable hypodermic needle configured to extend out of the housing, penetrate into the patient's skin, and retract into the housing. The injector assembly can comprise an array of polymeric, swellable microneedles. One or more arrays of polymeric, swellable microneedles can be included in the injector assembly. A first reservoir within the housing can contain a supply of the first drug. A first array of polymeric, swellable microneedles can be in interruptible fluid communication with the first reservoir. Similarly, a second reservoir can be provided within the housing, containing a supply of the second drug. A second array of polymeric, swellable microneedles can be in interruptible fluid communication with the second reservoir. Accordingly, the wearable device can be configured to deliver the first and second drugs from the first and second reservoirs, respectively, through first and second arrays of polymeric, swellable microneedles, respectively.

The wearable device can comprise a drug delivery system that includes a pump. The pump can be configured to pump the first drug, the second drug, or both, through the injector assembly and into the patient, through the patient's skin. The pump can comprise a piezoelectric pump, a squiggle motor, a medical pump patch, a thermal pump, a piston pump, an electromagnetic spring, a combination thereof, or the like.

The wearable device can comprise an adhesive layer and the adhesive layer can be attached to a bottom surface of the housing. One side of the adhesive layer can be attached to the bottom surface of the housing while the other side can be in the form of an outermost adhesive surface. The outermost adhesive surface can be configured to adhere the housing to the skin of a patient. Prior to use, the outermost adhesive surface can be protected by a releasable liner. The adhesive of the adhesive layer can comprise, for example, a pressure sensitive adhesive, and the liner can comprise, for example, a polymeric film such as a polyethylene film or a polytetrafluoroethylene film or coated sheet. The adhesive layer can have a hole formed therein and the hole can be aligned with the injector assembly so that the injector assembly can inject the first drug, the second drug, or both, into the patient's skin without needing to penetrate the adhesive layer. The releasable liner can be a protective liner and can cover a hole formed in the adhesive layer, if such a hole is provided.

The wearable device can further comprise an injector drive system. The injector assembly can comprise a retractable hypodermic needle and the injector drive system can comprise a battery, a battery-powered motor, and a drive train configured to extend the retractable hypodermic needle out of the housing and into a patient's skin. The injector drive system can be configured to retract the retractable hypodermic needle back into the housing after injecting the drug into the patient's skin. The wearable device can comprise an injector drive system and a drug delivery system, for example, wherein the drug delivery system comprises a pump and is configured to pump the first drug, the second drug, or both, through the retractable hypodermic needle.

The wearable device can comprise a drug delivery system that includes a first pump and a second pump. The injector assembly can comprise a first injector device and a second injector device. The first pump can be configured to pump the first drug through the first injector device and the second pump can be configured to pump the second drug through the second injector device. Such a device, and others as described herein, can be configured for the management of anemia, and methods of managing anemia are also provided according to the present invention. The first drug can comprise erythropoietin. The control system can comprise a microprocessor and a memory, the memory can have stored therein a plurality of hemoglobin values and a plurality of respective change values, each corresponding to a required change in erythropoietin administration rate. Each required change can be based on a hemoglobin value. A comparison of a determined hemoglobin value with the plurality of hemoglobin values stored in the memory can be made to determine a recommended required change in erythropoietin administration rate. The control system can be configured to determine a level of hemoglobin in a patient to which the wearable device is attached, and then compare the level of hemoglobin determined to hemoglobin values stored in the memory. The control system can also be configured to regulate the rate of injection of erythropoietin into the patient by changing the rate of injection of erythropoietin by a value corresponding to the required change value stored in the memory and that corresponds to the hemoglobin value determined. For the management of anemia, the first sensing system can comprise a pulse oximeter, a hematocrit sensor, a hemoglobin sensor, a blood pressure sensor, a heartbeat rate monitor, a combination thereof, or the like. The memory can have stored therein a three-dimensional matrix of evaluation triplets and an assigned value corresponding to each evaluation triplet. Each assigned value can correspond to a required change in a rate of injection of erythropoietin. As an example, the control system can be configured to calculate a first evaluation quantity ($O_2$ Sat) based on an amount of blood oxygen sensed by a pulse oximeter. The control system can further be configured to calculate a second evaluation quantity (Hemo) based on a level of hemoglobin sensed by a hemoglobin sensor. The control system can also calculate a third evaluation quantity (BP) based on a blood pressure sensed by a blood pressure sensor. The control system can be configured to form an evaluation triplet ($O_2$ Sat/Hemo/BP) from the first evaluation quantity, the second evaluation quantity, and the third evaluation quantity. The control system can be configured to compare the evaluation triplet thus formed to evaluation triplets stored in the memory. The control system can further be configured to regulate a rate of injection of erythropoietin by changing the rate of injection of erythropoietin by a value corresponding to a required change value stored in the memory, which required change value corresponds to the evaluation triplet formed. Such a wearable device, and others described herein, can comprise a transmitter configured to transmit a regulating signal to a remote device. The regulating signal can include information pertaining to the evaluation triplet formed by the control system. The remote device can comprise a mobile communications device, a cellphone, a smartphone, a tablet, a smartwatch, a fitness tracker, a physician network computer, a laptop computer, a desktop computer, a remote microprocessor, a remote central processing unit, a combination thereof, or the like. As an example, the wearable device can comprise a transmitter configured to transmit the first evaluation quantity, the second evaluation quantity, and the third evaluation quantity, via wireless live streaming, to a physician network computer.

The wearable device of the present invention can be part of a system that also includes a computer network, for example, comprising at least one physician network computer. The wearable device can comprise a transmitter configured to transmit information signals from the wearable device to a physician network computer. The transmitter can be configured to transmit, for example, first, second, and third evaluation quantities as described herein. One or more physician network computers, of a computer network, can be provided with a receiver, for example, an antenna, configured to receive information signals from the wearable device. The wearable device transmitter can be configured to transmit a blood oxygen saturation quantity, a hematocrit quantity, a hemoglobin quantity, a heartbeat rate quantity, and a blood pressure quantity, to one or more physician network computers. The wearable device can produce a glucose quantity and transmit a signal representing the glucose quantity to the network. Transmission of data from the wearable device to the network can occur via wireless live streaming, by sending and receiving packets of information, or when within range of a cellular tower. The network can further comprise a pharmacy computer.

For the management of anemia, the injector assembly of the wearable device can comprise a first injector device and a second injector device. The second injector device can supply an iron supplement. The second injector device can comprise an iontophoretic transdermal iron delivery patch. A fluid communication can be provided between a second reservoir and a second injector device comprising an iontophoretic transdermal iron delivery patch. The second reservoir can contain a supply of ferric pyrophosphate iron salt solution. A frangible seal can be provided between the second reservoir and an iron delivery patch. An interruptible fluid communication can be provided by a valve, for example, in the form of a piezoelectric clamp, so as to provide an interruptible fluid communication between the second reservoir and the second injector device.

The wearable device can comprise a battery and an iontophoretic transdermal iron delivery patch that comprises an electrode pair. The electrode pair and the battery can each be in electrical communication with the control system and the control system can be configured to control a flow of electrical current from the battery to the electrode pair, based on an iron control signal. The iron control signal can be received by the control system and can be indicative of a level of iron in a patient to which the wearable device is attached. The iron control signal can be generated by the first sensing system and received by the control system. The iron control signal can be wirelessly transmitted to a network, to a physician's computer, to a pharmacy computer, or to a combination thereof. The iron control signal can be downloaded from the wearable device via a micro USB port or another data transfer cable port, or the like.

The wearable device according to the present invention can be provided with sensors to monitor the amounts of drugs available in the device, for injection into a patient. The wearable device can comprise a first reservoir within the housing, which contains a supply of the first drug. The wearable device can comprise a second reservoir within the housing, which contains a supply of the second drug. A first drug level sensor can be provided and configured to sense the amount of the first drug in the first reservoir. The first drug level sensor can be configured to generate a first drug supply signal and a signal transmitter can be provided in the wearable device and configured to transmit the first drug supply signal to a remote device. The wearable device can comprise a second drug level sensor configured to sense the amount of the second drug in the second reservoir. The second drug level sensor can be configured to generate a second drug supply signal and a signal transmitter can be provided in the wearable device and configured to transmit the second drug supply signal to a remote device.

According to the present invention, a network of devices is also provided wherein at least one of the devices comprises a wearable device as described herein. Other devices connected to the network can include a physician computer processor, a pharmacy computer processor, a smartphone, a smart watch, a tablet computer, a laptop computer, a desktop computer, a server, or the like. The wearable device can comprise a transmitter configured to wirelessly transmit drug information pertaining to the amount of, expiration date of, or both, of a drug contained in the wearable device. The wireless transmission can be to a remote device on the network, for example, a physician computer processor can be included in the network and can comprise a receiver for receiving the drug information from the transmitter. The physician computer processor can also comprise a transmitter for transmitting prescription information that is based on the drug information. The physician computer processor can transmit the prescription information to a pharmacy computer processor on the network and the pharmacy computer processor can comprise a receiver for receiving the prescription information.

A method is also provided, according to the present invention, for maintaining a prescribed drug in a wearable device as described herein. The method can involve transmitting drug information from a transmitter of the wearable device to a physician computer processor. Some or all of the transmitting can occur wirelessly. The transmitting can comprise directly transmitting the drug information or indirectly transmitting the drug information through one or more intermediate devices. The method can involve receiving, at a physician computer processor, the transmitted drug information. Based on the drug information received, a physician can prescribe a prescription and transmit the prescription from a transmitter of the physician's computer processor to a pharmacy computer processor. The prescription can, for example, be for a drug for the treatment of anemia. The prescription can be based, at least in part, on the drug information transmitted by the wearable device. The method can further involve receiving, at the pharmacy computer processor, the prescription transmitted from the physician computer processor. The method can involve preparing one or more reservoirs or patches of respective drugs to fulfill the transmitted prescription. The one or more reservoirs or patches can be configured to be inserted into and connected to the wearable device. The method can further comprise delivering the one or more reservoirs or patches to a patient for whom the wearable device has been prescribed.

The wearable device can further comprise a memory and the control system can be configured to store, in the memory, injection history information. Injection history information that can be stored in the memory can pertain to the amount of drug injected and the time of the injection, for injections made by the wearable device. The wearable device can further comprise a transmitter and the transmitter can be configured to wirelessly transmit the injection history information to a remote device, such as a physician computer processor. A network comprising the wearable device and a physician computer processor is also provided wherein the physician computer processor can comprise a receiver for receiving injection history information from the transmitter of the wearable device. The wearable device can further comprise a micro USB port or another data transfer cable port from which the injection history information can be downloaded, via wired connection, to a remote device.

A method of reporting information pertaining to the use of the wearable device is also provided and the method comprises transmitting injection history information and patient parameter information. At least some of the transmitting can occur wirelessly and the transmitting can comprise directly transmitting the injection history and patient parameter information or indirectly transmitting the injection history and patient parameter information through one or more intermediate devices. The method can comprise receiving, at the physician computer processor, the transmitted injection history and patient parameter information, and, based on the information, prescribing operating instructions for operating the wearable device. The method of reporting can further comprise transmitting operating instructions to the control system for the control system to use in operating the wearable device.

The wearable device of the present invention can comprise a drug infusion device, such as "pump patch," that is lower in cost and somewhat more convenient and comfortable to use than conventional drug delivery pump mechanisms.

The device can comprise a flexible pump patch designed for a patient to wear on the patient's body. The pump patch can have a reservoir of a medication or drug and allow for delivery of the medication or drug to the patient. Examples of pump patches can be found in U.S. Patent Application Publications Nos. US 2010/0292632 A1, US 2014/0074062 A1, US 2017/0056585A1, US 2017/0157329 A1, US 2019/0015581 A1, US 2019/0091457 A1, US 2019/0214967 A1, and US 2019/0269862 A1, which are incorporated by reference herein in their entireties.

Figure 10:
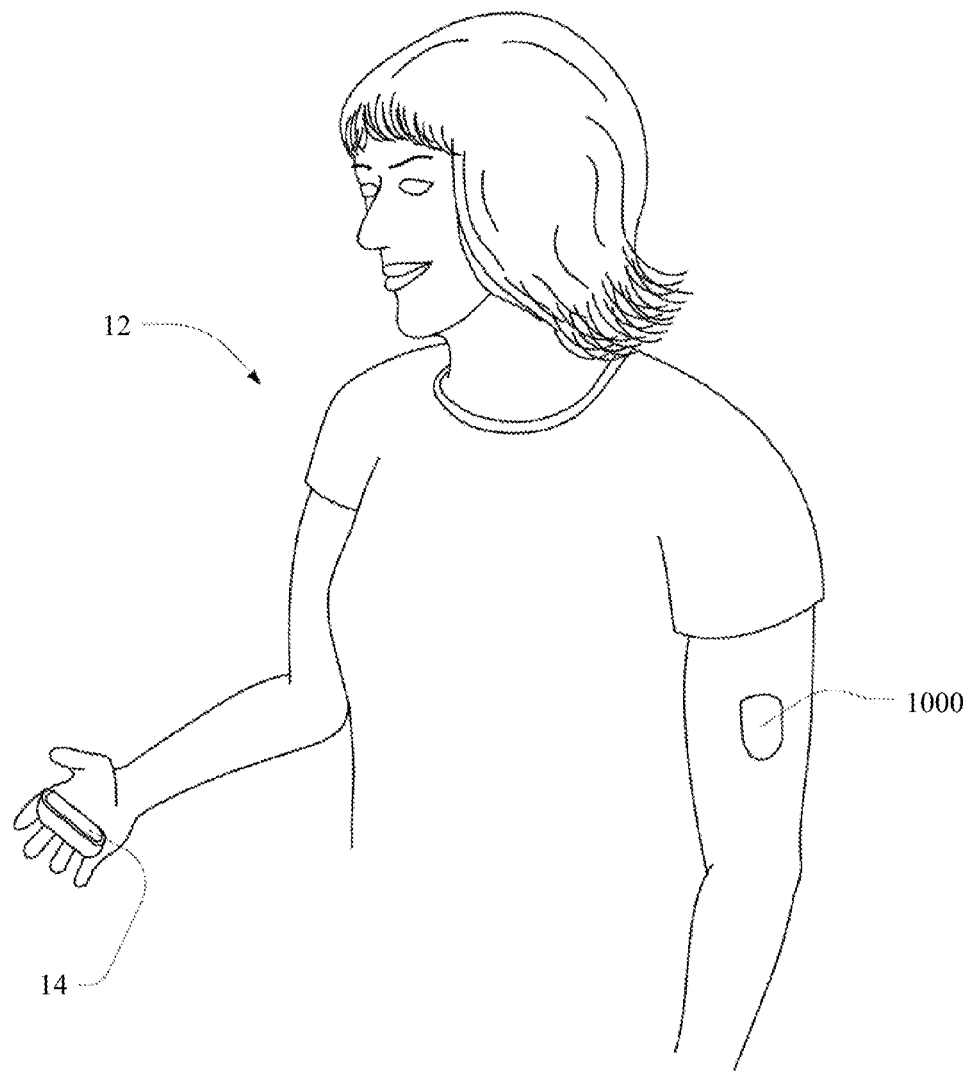
FIG. 10 is an illustration of a patient having a wearable device of an embodiment of the present invention, adhered to her arm, and holding a hand-held remote controller for controlling the wearable device.

The drawings appended hereto include FIG. 10 that shows a wearable device 1000, according to various embodiments of the present invention, adhered to the upper arm of a patient. It is to be understood, however, that the wearable device according to the present invention can be adhered to any suitable location on the patient, including, for example, the back, hip, belly, chest, shoulder, thigh, torso, or forearm. The wearable device can be adhered adjacent to a site that would be suitable for a bone marrow aspiration procedure, which can be a very effective site for drug delivery. These sites can include at the back of the hipbone, at the posterior iliac crest, or at the sternum.

Figure 2:
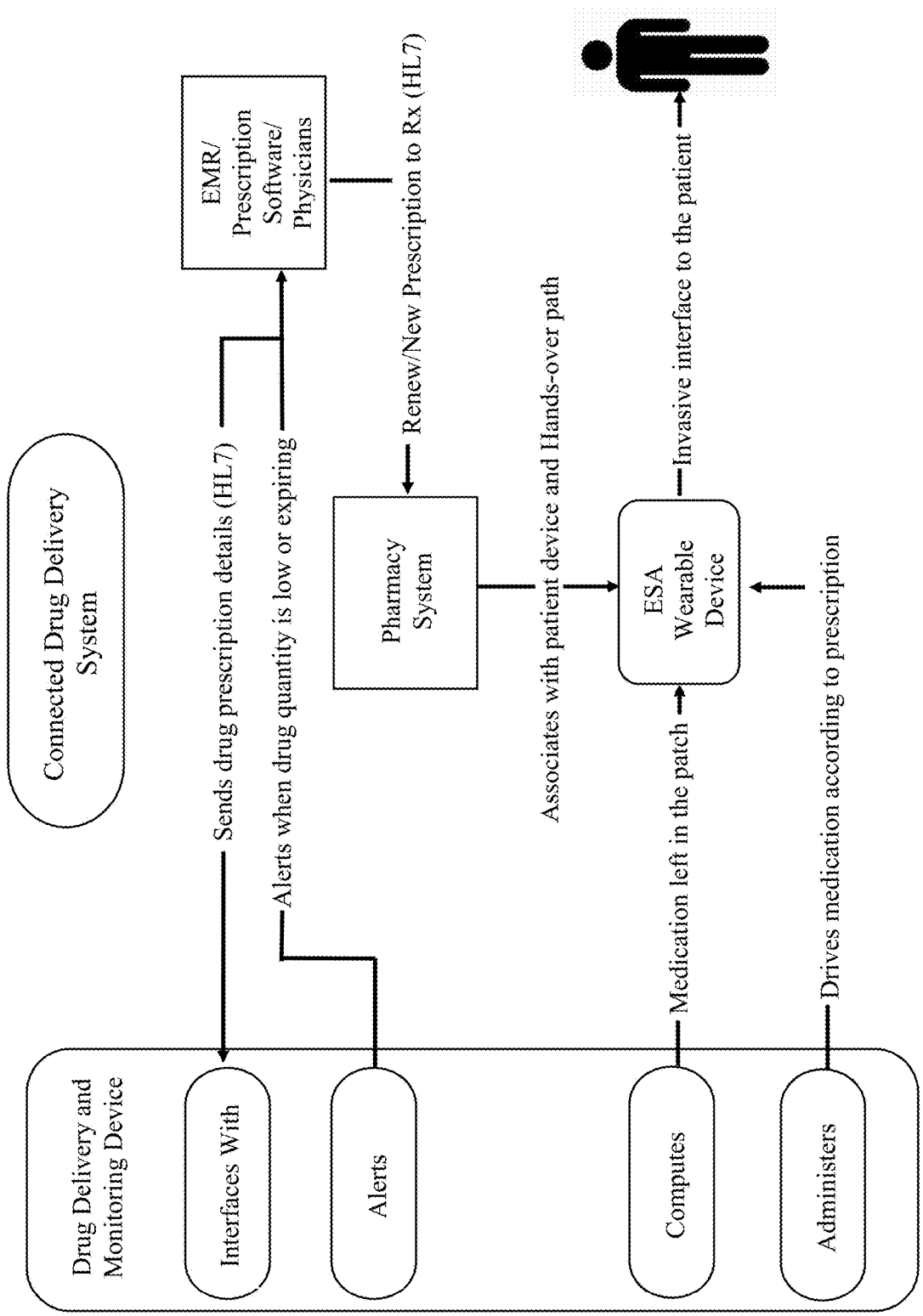
FIG. 2 is a flow diagram showing the various steps and orders that are followed according to various methods carried out by a connected drug delivery system according to an embodiment of the present invention.

FIG. 2 is a flow diagram showing the various steps and orders that are followed according to an exemplary method carried out by a connected drug delivery system according to an exemplary embodiment of the present invention. As shown in FIG. 2, a wearable device denoted as a Drug Delivery and Monitoring Device receives drug prescriptions details, alerts a physician when a drug quantity is low or expiring, computes the amount of medication left in the device, and administers medication from the device to the patient according to the prescription.

Figure 3:
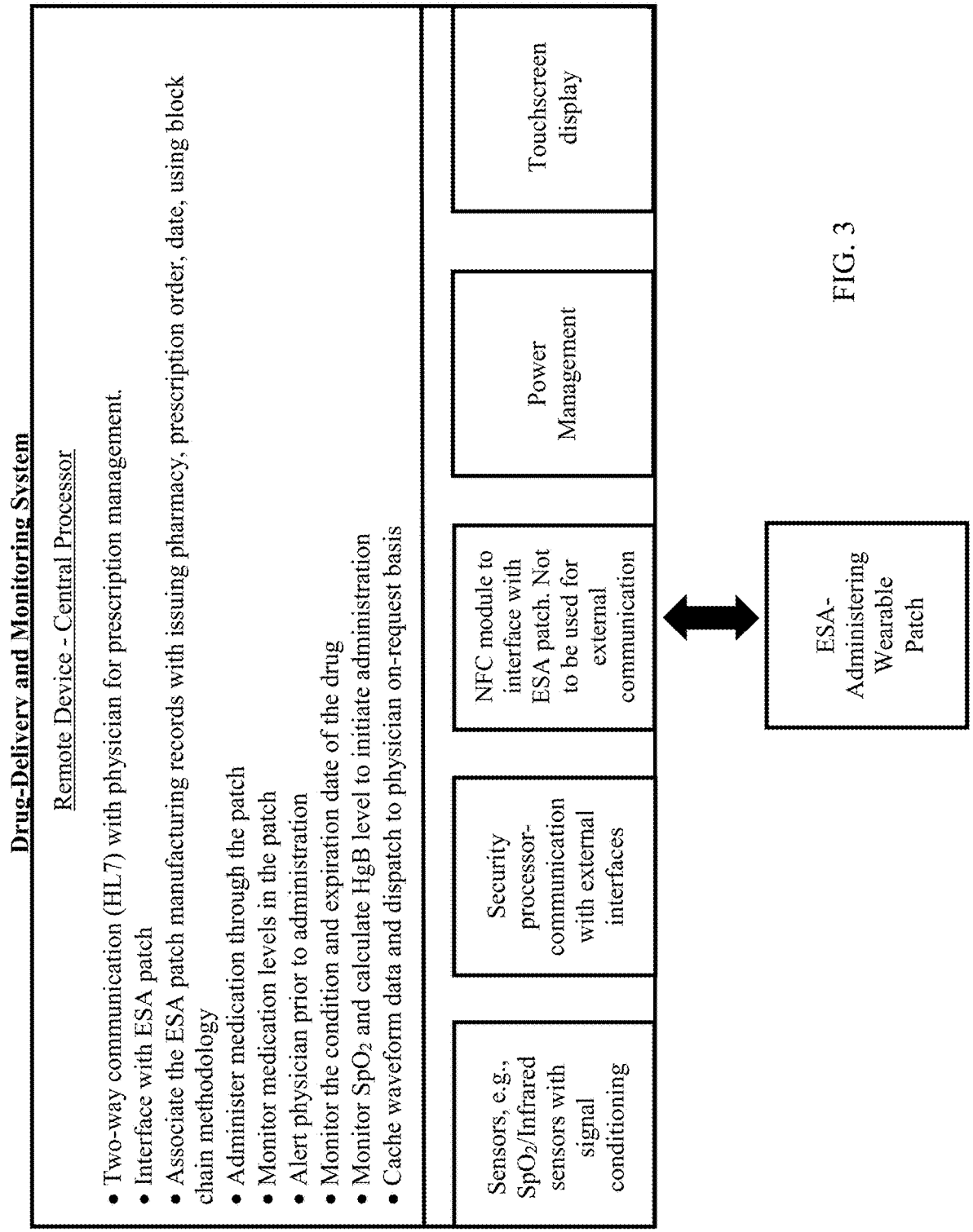
FIG. 3 is a schematic diagram showing a drug delivery and monitoring system according to various embodiments of the present invention, including a remote device and a wearable device in the form of a patch, and showing the connectivity between components integrated in the remote device and components integrated in the ESA-administering wearable patch.

FIG. 3 is a schematic diagram showing the connectivity between components of an ESA-administering wearable device in the form of a wearable patch, and a remote device, in a system according to various embodiments of the present invention. The diagram shows the connectivity between components integrated in the remote device and components integrated in the wearable patch. FIG. 3 sets out various functions of a central processor in the remote device, which can communicate with, for example, an integrated circuit incorporated into the wearable patch.

Figure 4:
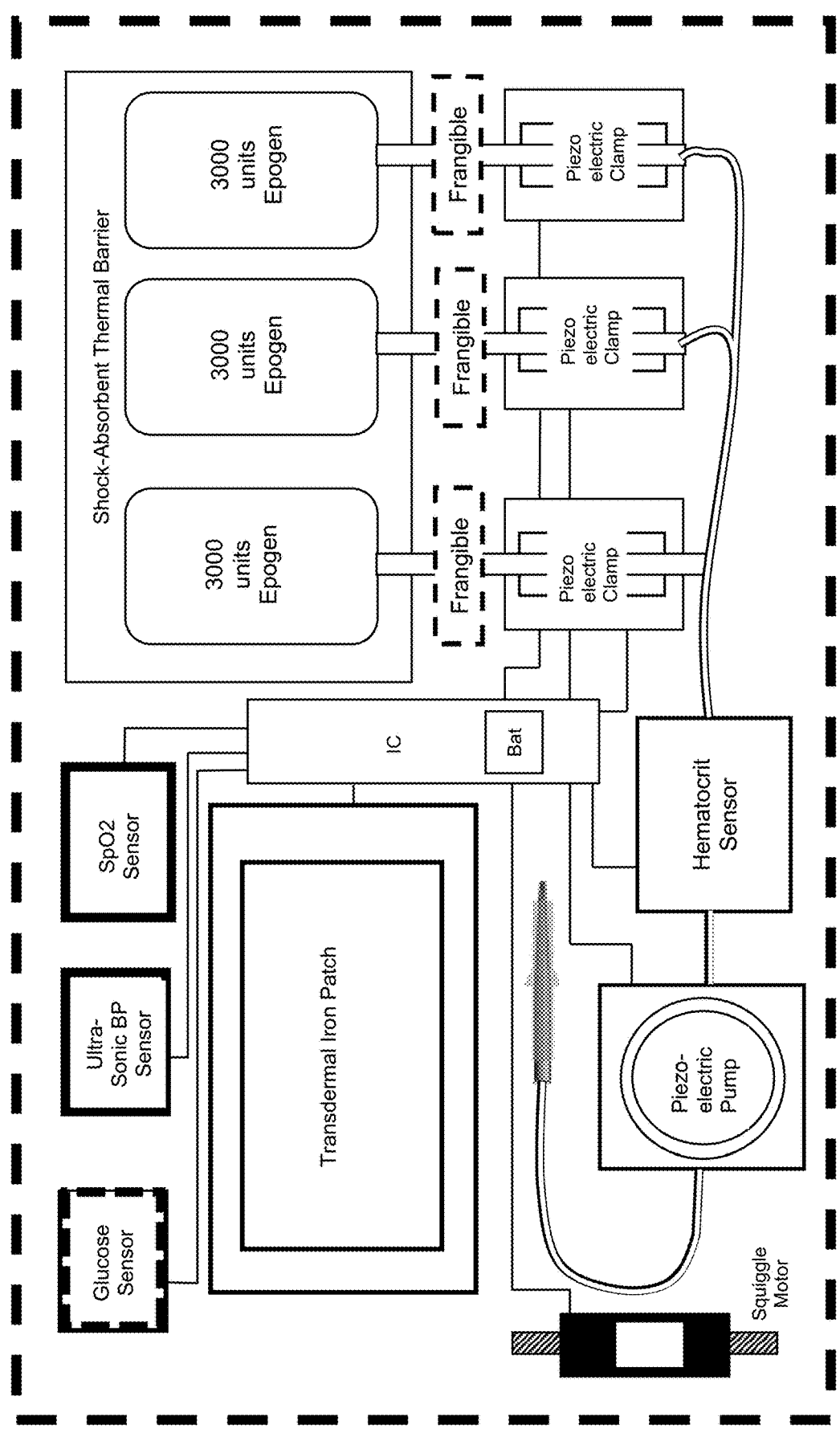
FIG. 4 is a diagram of an exemplary layout for a wearable device according to various embodiments of the present invention.

FIG. 4 shows a layout of a wearable device according to an exemplary embodiment of the present invention. For clarity, simple electrical and data transfer leads are shown connected to an integrated circuit shown as IC. Through one or more leads, each component of the device can be connected to integrated circuit IC. Wireless connections can also or instead be used. A battery (Bat) is shown connected to integrated circuit IC. Battery Bat can be a lithium ion battery, rechargeable, replaceable, disposable, a combination thereof, or the like. Each piezoelectric clamp can act as a valve to meter the flow of a drug, such as Epogen, from the respective reservoir to the piezoelectric pump. The frangible seals can be broken as soon as the respective Epogen reservoir is installed, broken in series based on suction created by the piezoelectric pump, broken as needed by a user upon notification sent to a remote device, a combination thereof, omitted altogether, or the like. Once a first of the Epogen reservoirs is depleted or emptied, the integrated circuit can then trigger the next piezoelectric clamp to open enabling access to a second of the reservoirs and enabling rupture of a second respective frangible seal.

The wearable device can include an insulating layer or layers. The layer or layers can prevent over-heating of the device. For example, the insulating layer can prevent the device from achieving temperatures above 83° F. The wearable device can be kept cool by any suitable cooling means. An exemplary cooling means that can be used onboard the wearable device is a micro cooling fan from Sunon, for example, the Ultra Micro Cooling Device by Sunon, which is described at www.sunon.com. Another exemplary cooling means is a device as described by Michael Irving in "Twist fridges' could cool down by unraveling fibers," at New Atlas (ISO 18562) VOC & Particle Testing, Oct. 14, 2019. The wearable device can include a stabilizing medium to prevent shock to the device. The wearable device can include a shock-absorbent thermal barrier, for example, at least underneath the drug reservoir or reservoirs.

The wearable device can be configured to perform glucose sensing. Such sensing can be accomplished with a Biolinq device, for example, using the using the device and method described at https://www.biolinq.me/. Glucose sensing can be accomplished with a device and method as described for the Omnipod DASH Insulin Management System device available from Insulet Corporation. Glucose testing can be accomplished with the HemoCue system, for example, the HEMOCUE Hb 801 System available from HemoCue AB of Angelholm, Sweden. As an alternative, the wearable device can communicate with a glucose testing means, for example, a HemoCue system. A description of the HEMOCUE Hb 801 System can be found at https://www.hemocue.us/en-us/solutions/hematology/hemocue-hb-801-system. Further, glucose testing can be carried out with the Dexcom Continuous Glucose Sensor available from Dexcom, Inc. An example of the glucose sensor can be a sensor available from Dexcom, Inc. found at http://www.dexcom.com/.

RileyLink is one way to establish communication between the wearable device and a receiving device, for example, a receiving device in the form of a smartphone. RileyLink can also be used establish communication between other components of the wearable device and the receiving device. The RileyLink system can, for example, use the RileyLink 916 MHz Antenna Kit or the 433 MHz Antenna Kit, available from GetRileyLink.org of Cumming, Georgia.

Blood pressure sensing can be accomplished with a device and method as described in *Wearable Ultrasound Patch Monitors Blood Pressure Deep Inside Body* by Labios, UC San Diego News Center, UC San Diego, Sep. 12, 2018. The device can be a piezoelectric blood pressure sensor. Hemoglobin monitoring can be accomplished in a non-invasive manner with a device and method as described in Joseph et al., *Non-invasive hemoglobin monitoring,* International Journal of Surgery, Volume 33, Part B, September 2016, Pages 254-257. The wearable device can also measure hematocrit values. An example of a hematocrit measuring device and method is that described by Ekuni et al. in *Noninvasive and Continuous Hematocrit Measurement by Optical Method without Calibration,* Electronics and Communications in Japan, Volume 99, Issue 9, Aug. 12, 2016 (Wiley Online Library).

The wearable device can include a transdermal iron patch. An example of a suitable transdermal iron patch is the patch available from Fe3 Medical found at https://www.fe3medical.com/. The transdermal iron patch can use iontophoresis electrodes, such as those described at the website https://media.lanecc.edu/users/howardc/PTA101/101IontoPhono/101IontoPhono_print.html. The Epogen reservoirs or other drug reservoirs can be provided with thermal and shock barriers, for example, underneath or encompassing the reservoirs. A daylight sensor, internal clock, or both can be incorporated into the wearable device so that the patient is injected at the optimum time of day. The optimum time can be, for example, when the patient is active, so injection discomfort is less noticeable. The optimum time can be, for example, when the patient is not sleeping. The optimum time can be, for example, determined based on heart rate detected by a heart rate monitor. A GPS monitor, locator beacon, or both can be incorporated into the wearable device, which can be especially useful for children or the elderly and can assist in finding the device or the patient, if lost. The wearable device can include thermal sensor to monitor medication temperature and a method to cool the medication if it gets too hot, for example, even if the ambient temperature becomes too hot. The thermal sensor can take the form of an alert that would notify the patient of the need to move to someplace cooler. Cooling devices can be incorporated, as described herein, and can be triggered based on a signal sent from a thermal sensor. An on-device cooling fan can be incorporated, as can a heatsink, a mini-compressor, a compressed gas venting device, a device that causes twistocaloric cooling. Twistocaloric can be enabled through the incorporation and use of a Squiggle motor or other micro motor configured to re-twist an array of fibers after the array has been untwisted to effect cooling and after the wearable device has cooled sufficiently to reset a twistocaloric fiber array.

Figure 5:
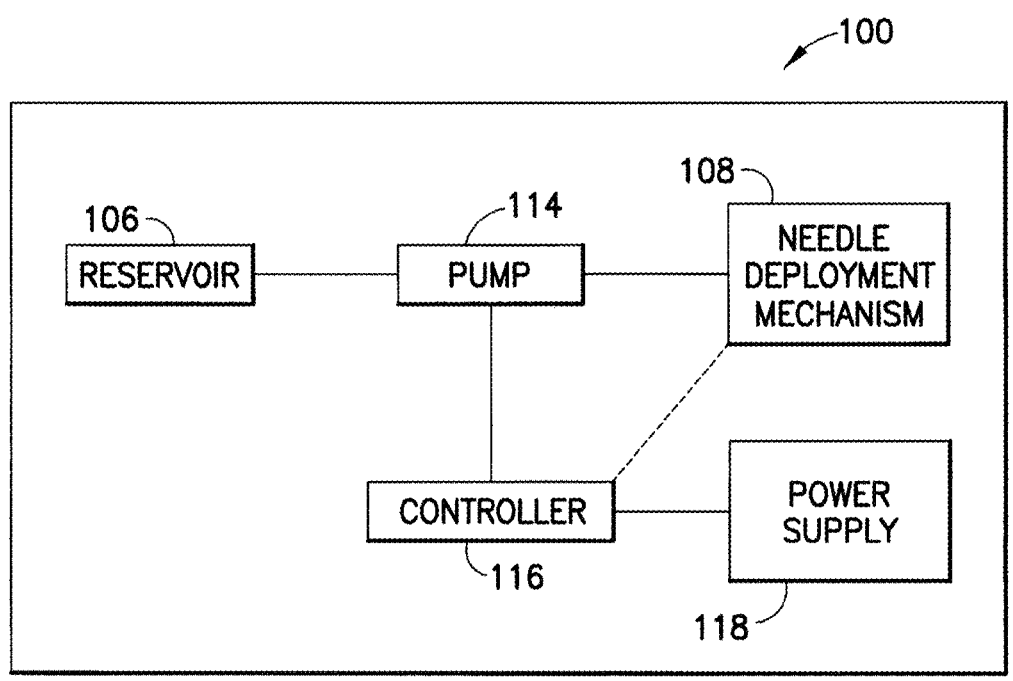
FIG. 5 is a diaphragm showing an exemplary layout of basic components of a device according to the present invention.

FIG. 5 shows a wearable pump patch that can be used as part of a wearable device of the present invention. As seen in FIG. 5, the pump patch generally comprises a housing for a flexible drug reservoir 106 or other container for supplying a drug. An infusion needle deployment mechanism 108 is provided along with a pump mechanism 114 or fluid metering device for controlling the delivery of the drug into the patient's body through an infusion needle provided in the infusion needle deployment mechanism 108. Pump patch 100 also preferably comprises a microprocessor or controller 116 for controlling the infusion needle deployment mechanism 108 and pump mechanism 114 as well as for monitoring and controlling other operations and systems of pump patch 100. A power supply 118 is also included, such as any known power source, including, but not limited to, a disposable or rechargeable standard battery, capacitor, or energy harvesting system such as that disclosed in U.S. Pat. No. 8,939,928 B2 to Savoie et al., which is incorporated herein by reference in its entirety.

According to various embodiments, the pump patch comprises a chassis. The chassis can comprise at least a first frame flexibly connected to a second frame for positioning a first system component in the first frame and a second system component in the second frame such that the first and second components can be positioned relative to each other in the housing. The pump patch further comprises an infusion needle deployment mechanism actuated by a push button deployable within the housing. The needle deployment mechanism can comprise a spring disk for driving the infusion needle into the patient. The needle deployment mechanism can comprise a torsion spring actuated by a finger lever for driving the infusion needle into the patient. The needle deployment mechanism can comprise a needle carriage and a cannula carriage initially engaged with each other for driving a flexible cannula into the user using an insertion needle, and a spring member for withdrawing the insertion needle from the user upon insertion of the flexible cannula into the user. A similar needle carriage and biosensor carriage can be provided for inserting a biosensor into the user with the aid of an insertion needle, and the needle can be withdrawn from the patient after insertion of the biosensor. The pump patch can also comprise a mechanism for manually actuating a bolus dose by applying a force to a specific area on the upper portion of the housing, and a mechanism for deploying a transcutaneous analyte sensor for the purpose of determining a physiological indicator.

Exemplary embodiments of a pump patch 100 to be used as, with, or in a wearable device in accordance with the present invention are illustrated in FIGS. 6-9. Each of the exemplary embodiments depicted in FIGS. 6-9 comprises flexible upper and lower covers, shown respectively as 202 and 204 in FIG. 6, as 302 and 304 in FIGS. 7A and 7C, as 402 and 404 in FIG. 8, and as 502 and 504 in FIG. 9A. In exemplary embodiments of the present invention, the upper and lower covers make up an external shell or housing for pump patch 100. Each of the upper and lower covers is preferably constructed from thin flexible polymers, such as polyethylene (PE), polypropylene (PP), or polyvinyl chloride (PVC). These materials are exemplary and are not intended to be limiting, and one of ordinary skill in the art will recognize that any suitable material for providing a thin flexible housing for the components of pump patch 100 can be used. The upper and lower covers are preferably substantially similar in shape, so as to have matching or near matching perimeters. In an exemplary embodiment, the upper and lower covers are sonically welded together along the perimeter of each to securely encapsulate the components of pump patch 100. The lower cover is preferably affixed to the patient's skin via any well known, long-lasting adhesive layer 210 that is safe for skin contact with the user. As the lower cover of pump patch 100 is affixed to the user, the lower cover conforms to the user and advantageously permits flexure of the entire pump patch 100. The upper cover is preferably designed to minimize imparting resistance to the flexure and conformity of pump patch 100. A housing for pump patch 100, constructed in this manner, is very thin, flexible and conformal to each patient's unique body shape. The minimal thickness and optimal flexibility of pump patch 100 affords the user a level of convenience, versatility and comfort.

Figure 6:
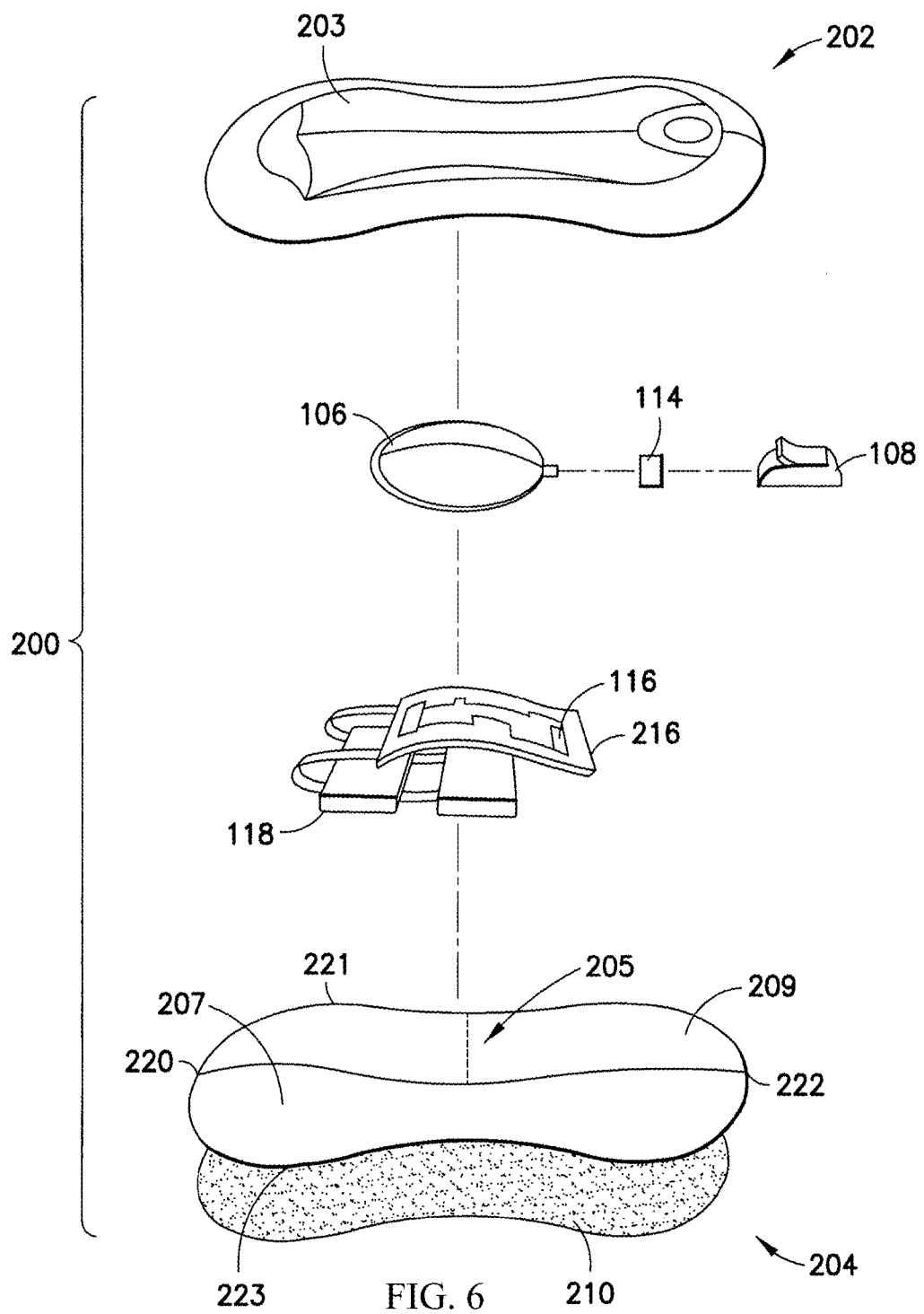
FIG. 6 is an exploded view of a wearable device according to various embodiments of the present invention.

FIGS. 6 and 7A-7C illustrate first and second exemplary embodiments of wearable device 100, respectively. Each provides two-dimensional conformity and flexibility in accordance with the present invention. The embodiment depicted in FIG. 6 is an elongate flexible wearable device 200 that realizes a minimal thickness, but also provides increased surface area for skin adhesion to a user. The design of flexible upper cover 202 and flexible lower cover 204 provide increased conformity to cylindrical shapes, such as a user's arm. Flexibility and conformity of wearable device 200 shown in FIG. 6 is increased by providing a "waist" 205 or reduced dimension of the mid-section of the elongate upper and lower covers. The wearable device 200 has a length dimension defined as the longest dimension extending from a first edge 220 of the cover to a second opposite edge 222 of the cover. The wearable device 200 has a width dimension defined as a longest dimension that is perpendicular to the primary dimension and spans from a third edge 221 to a fourth edge 223 of the cover opposite the third edge. The width of the device 200 is preferably contoured to be narrower at a midsection or "waist" 205. In the embodiment shown, the waist dissects the device 200, forming a first section 207 and a second section 209 opposite first section 207, that are preferably symmetrical about the waist, such that the first and second sections are of a similar shape and dimension.

The overall shape of upper cover 202 and lower cover 204 for wearable device 200 in an exemplary embodiment illustrated in FIG. 6, is not specifically limited to the shape depicted. Alternate shapes and relative dimensions of upper cover 202 and lower cover 204, suitable for use in this embodiment, will be understood by one of ordinary skill in the art. For instance, in another embodiment, instead of providing the "waist" 205 or reduced section midway along the length dimension of the upper and lower covers, as shown in FIG. 6, the flexible upper and lower covers can comprise at least one waist section at any point along the length dimension. This waist section preferably comprises a dimension that is perpendicular to the length dimension and less than the width dimension. In such an embodiment, it is not necessary that the upper and lower covers comprise a first and second section symmetrical about the at least one waist section, or that the waist section even dissects a first section and a second section equally. One of ordinary skill in the art will understand that any shape of a flexible upper and lower cover, 202 and 204, can be suitable for wearable device 100 in the first exemplary embodiment.

Exemplary embodiments of the present invention, as illustrated in FIGS. 6-9, provide not only a flexible housing for wearable device 100, as discussed above, but also preferably utilize flexible and low profile components within the housing to be specifically described further below, such as a flexible reservoir 106, flexible circuit board 216, flexible power supply 118, and flexible electrical conductors between components. The device can comprise a low-profile pump mechanism 114 and a low-profile infusion needle deployment mechanism 108. The profile of wearable device 100 can range in thickness from 0.2 inches to 1.25 inches, but in some cases can be no greater than 0.75 inches, depending on the specific functionality of the device. The profile can depend on whether the device is "smart", pre-programmed, or "simple," as well as the specific components chosen for needle deployment mechanism 108 and fluid metering mechanism 114, and the arrangement of such components. The specific components illustrated in FIG. 6 are not limited to this exemplary embodiment of the present invention and one of ordinary skill in the art will recognize that any combination and arrangement of components can be utilized in each of the exemplary embodiments illustrated and described with respect to FIGS. 6-9.

Figure 7A:
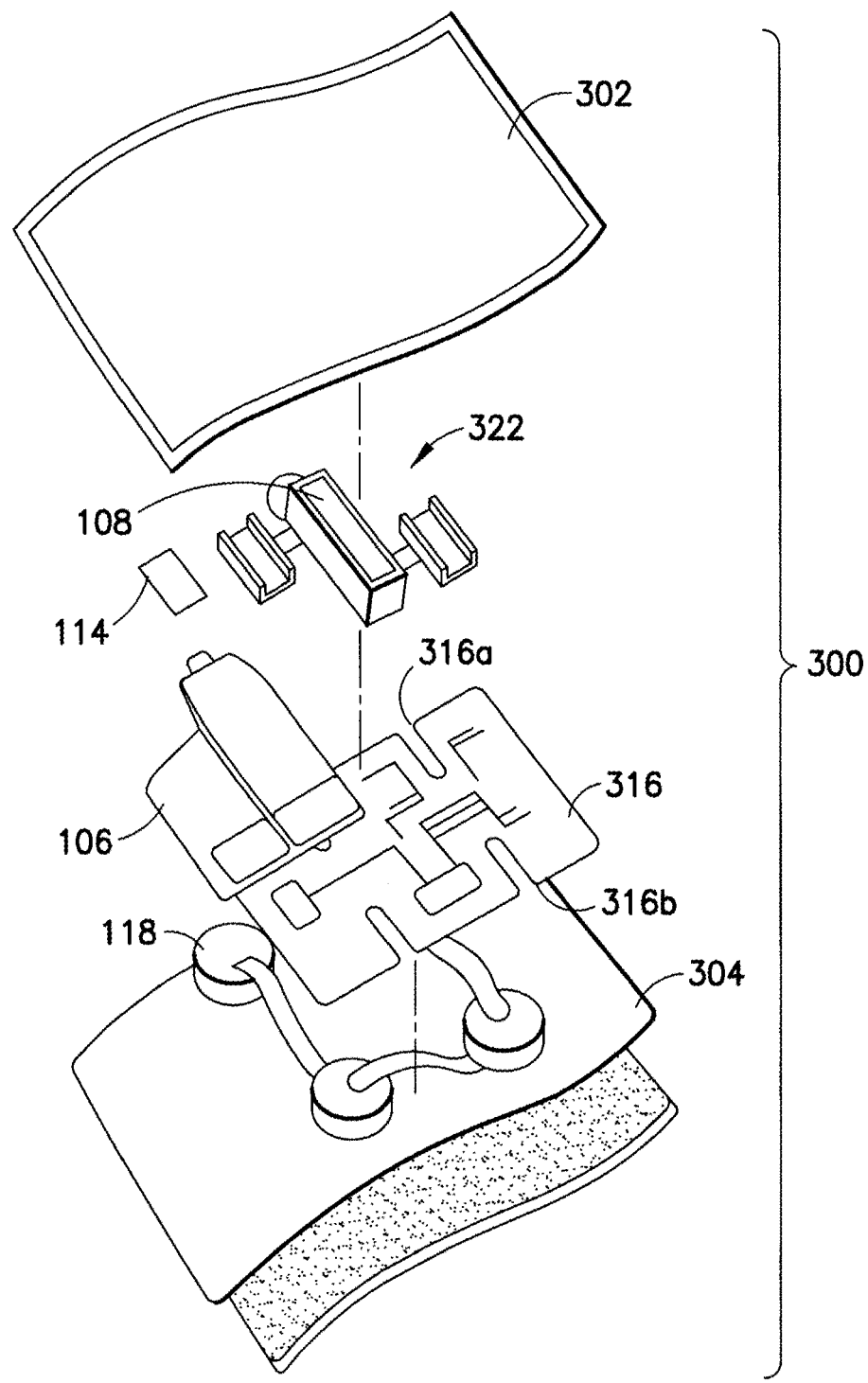
FIG. 7A is an exploded view of a wearable device according to various embodiments of the present invention.
Figure 7B:
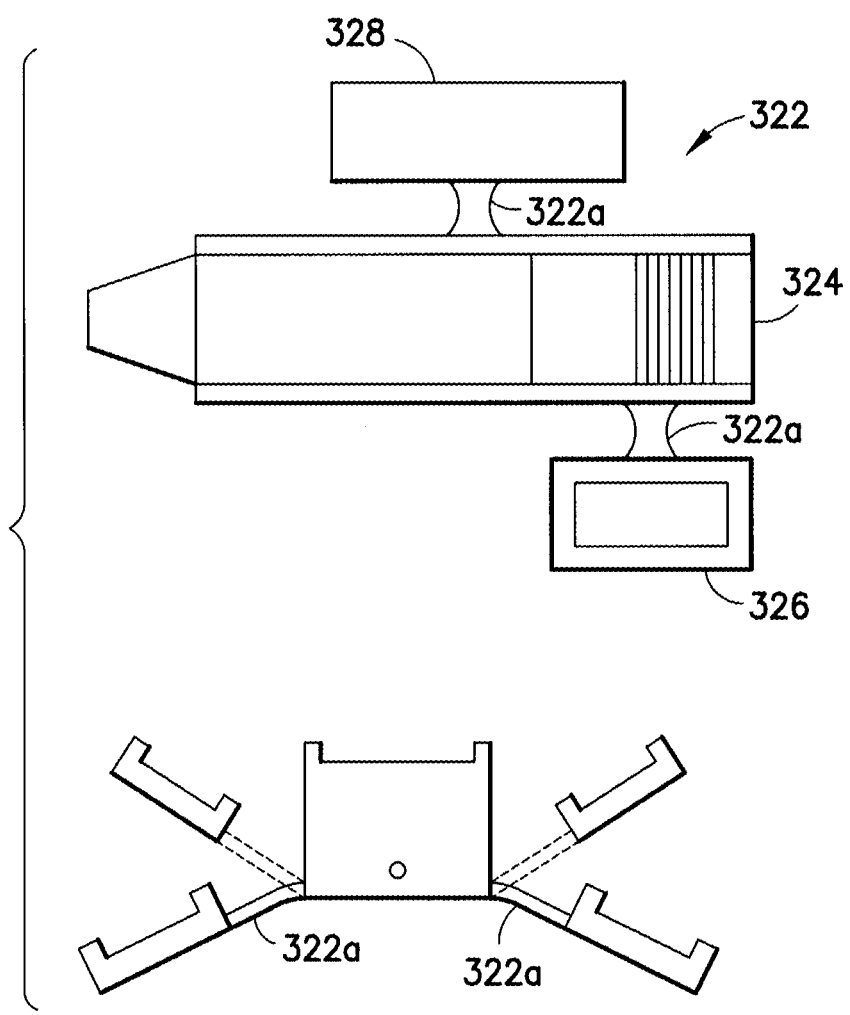
FIG. 7B is a top view and back end view of inner components of the wearable device shown in FIG. 7A.
Figure 7C:
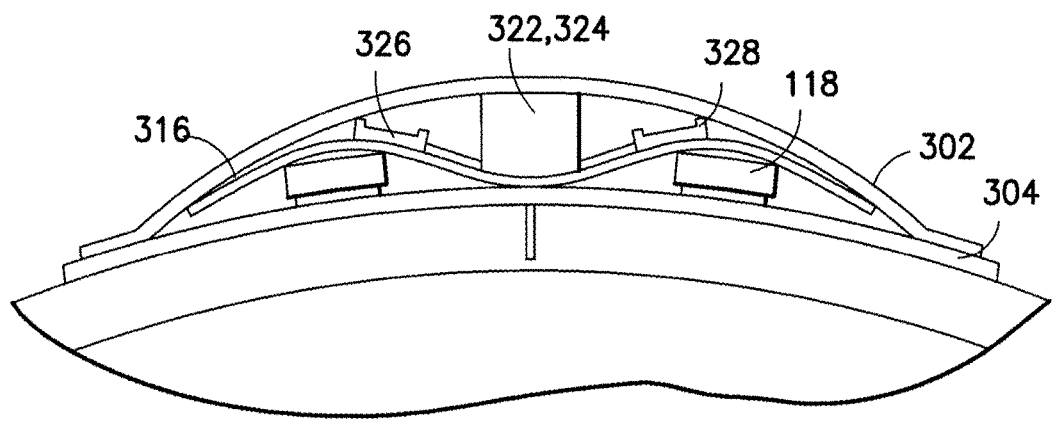
FIG. 7C is an end view of the wearable device shown in FIG. 7A, assembled.

The flexible and conformal wearable device 300 illustrated in FIGS. 7A-7C, is formed into a substantially rectangular package that resembles a common bandage, with a reduced surface area of coverage but increased thickness relative to the embodiment illustrated in FIG. 6. Flexible upper cover 302 and flexible lower cover 304 preferably provide optimal flexibility and conformity, as discussed above. Since the overall surface area or footprint of the flexible upper cover 302 and flexible lower cover 304 in this embodiment are reduced, it is not necessary to provide a reduced "waist" or midsection for aiding in conformity or flexibility. Due to the reduced surface area of wearable device 300, however, several of the desired components can be stacked or arranged on top of one another, as shown in FIG. 7C, resulting in the increased thickness of wearable device 300. To maintain overall flexibility and conformity of wearable device 300, the arrangement of the components should preferably not inhibit the desired flexure of wearable device 300, as will be described in further detail below.

The exemplary embodiment illustrated in FIG. 7A provides an exemplary flexible printed circuit board (PCB) 316 and a flexible chassis 322 for providing a flexible arrangement of the specific system components. The exemplary embodiment of a flexible printed circuit board 316 for use in this and other exemplary embodiments is shown in FIG. 7A. Flexible PCB 316 is modified in this embodiment to include slots, recesses or cutouts, 316a and 316b along the outer perimeter of PCB 316, as shown. This modification provides an additional degree of flexibility for the PCB 316 at locations that are preferably located between rigid system components, so as to enable the PCB to flex as necessary based on the close positioning of the other system components, as shown in FIG. 7C. It should be understood by one of ordinary skill in the art that the embodiment shown in FIGS. 7A-7C is provided merely for illustration, and to help understand the concepts which enhance the flexibility and conformity of a wearable device. The number of cutouts, 316a and 316b, the dimensions of such cutouts, and the placement of the cutouts on the PCB 316 are preferably selected based on the specific number and layout of components in a particular embodiment and are not limited by the exemplary embodiment illustrated in FIG. 7A.

FIGS. 7A and 7B illustrate a flexible chassis 322 for use in exemplary embodiments of the present invention. For efficient operation of wearable device 300, it is preferred that at least the reservoir 106, pump mechanism 114 and infusion needle deployment mechanism 108 all be located reasonably adjacent to each other. However, arranging such components too closely can result in an undesirable rigidity in the overall flexure of wearable device 300. Flexible chassis 322, as shown in FIG. 7B, is provided to preferably house at least a low-profile needle deployment mechanism 108 and pump mechanism 114. Chassis 322 comprises at least a first and second frame, 324 and 326, for holding the respective components in position relative to each other. A third optional frame 328 is shown, which in some embodiments can house a second needle deployment mechanism, a transcutaneous analyte sensor or biosensor, or any other components as will be understood by one of ordinary skill in the art. FIG. 7B illustrates how each of the respective frames, 324, 326 and 328, are maintained in relation to each other by flexible joints 322a molded to each of the connected frames. The interconnection of the system components using flexible joints 322a on chassis 322 serves to effectively hold the respective system components in relation to each other, while providing flexibility between the components of wearable device 300. FIG. 7C is a cross section of wearable device 300, illustrating the relative positioning and flexure of chassis 322 and PCB 316, in an exemplary embodiment of the present invention. One of ordinary skill in the art will appreciate that the relative dimensions and number of frames flexibly interconnected to each other are not limited by the illustrations in FIGS. 7A-7C and are merely provided as examples.

Figure 9B:
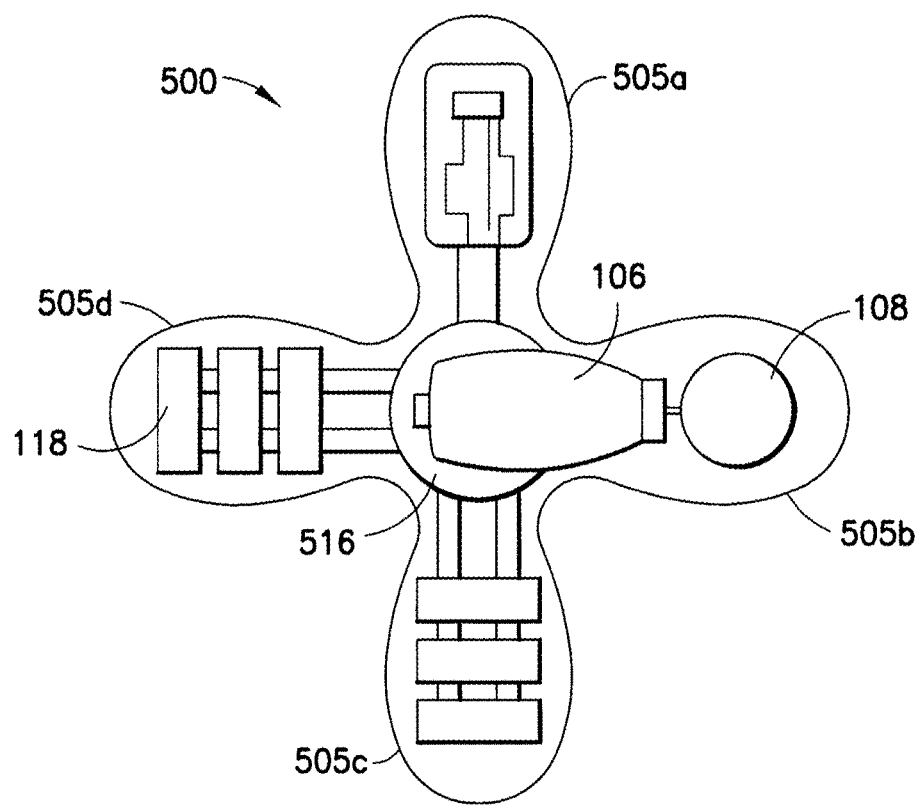
FIG. 9B is a top view of the wearable device shown in FIG. 9A, assembled.
Figure 8:
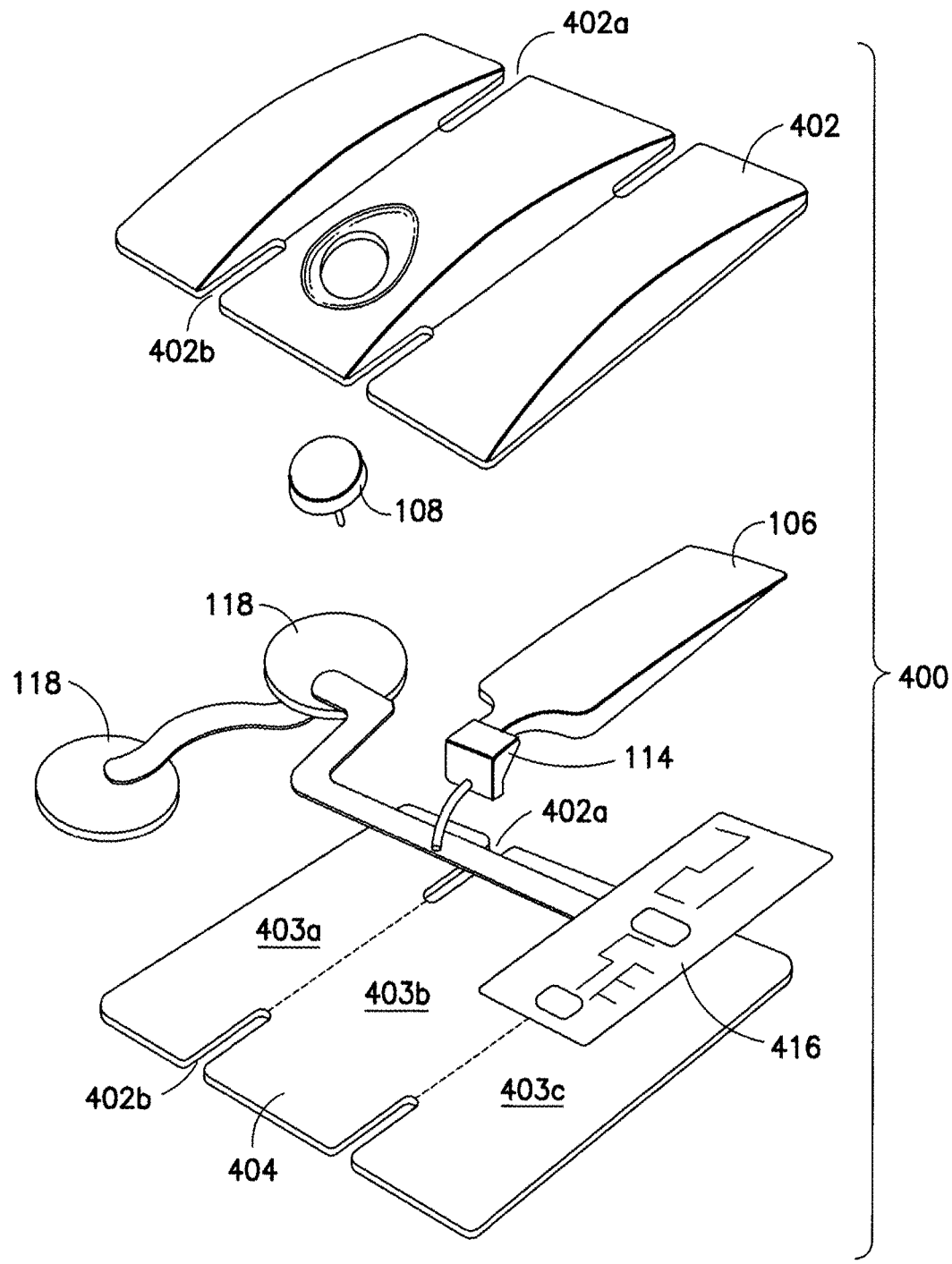
FIG. 8 is an exploded view of a wearable device according to various embodiments of the present invention.
Figure 9A:
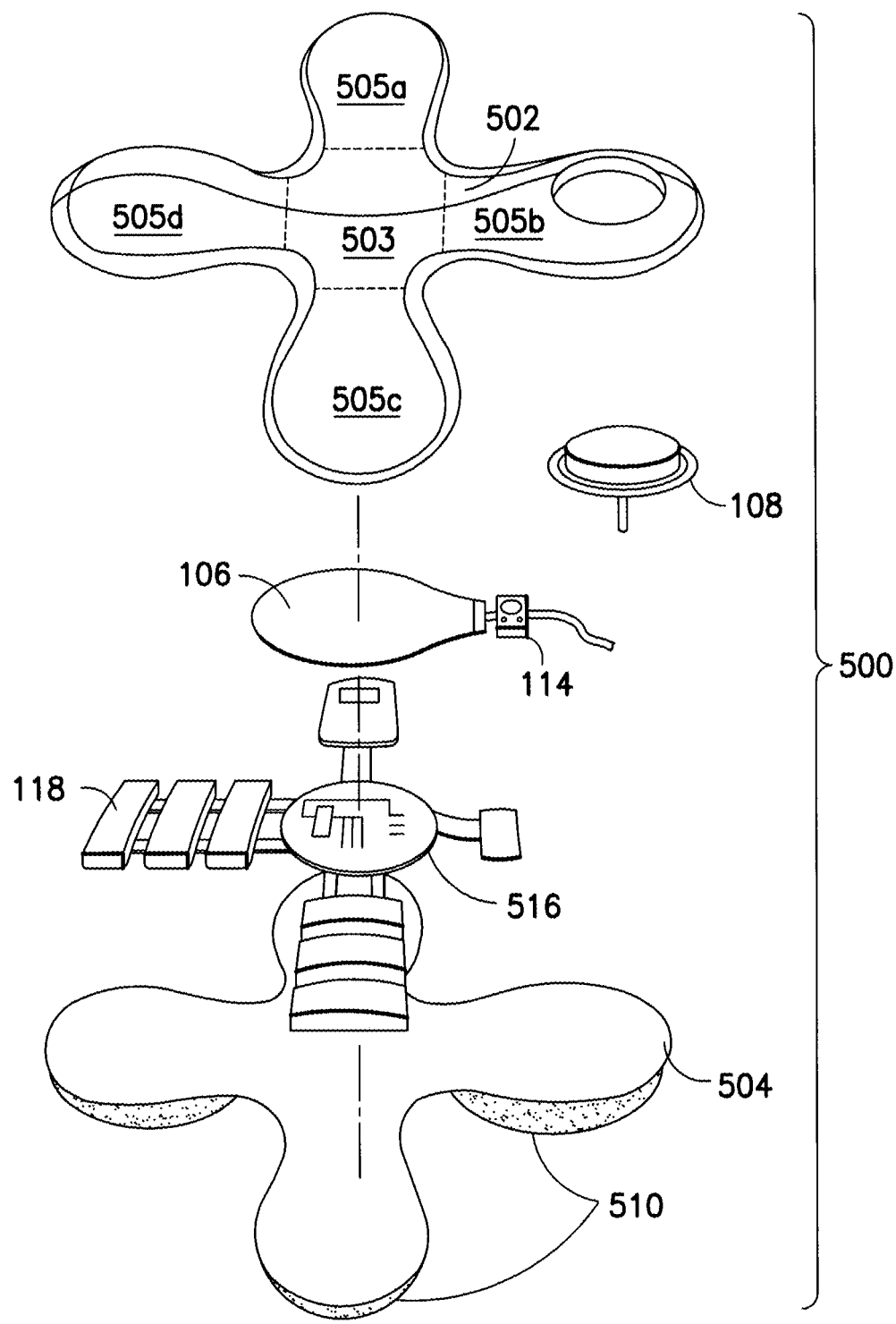
FIG. 9A is an exploded view of a wearable device according to various embodiments of the present invention.

FIGS. 8 and 9A-9B illustrate third and fourth exemplary embodiments, respectively, of wearable devices 400 and 500, respectively, that provide additional degrees of flexibility for easily conforming to complex shapes. Similar to the modification of PCB 316 in FIGS. 7A-7C, the flexible upper and lower covers of wearable device 400, in the exemplary embodiment shown in FIG. 8, can be designed with slits, cutouts, or recesses, 402a and 402b, along the perimeter of each. The number, size, and placement of recesses 402a and 402b illustrated in FIG. 8 is merely exemplary. The upper and lower covers, according to this exemplary embodiment, can comprise at least one inwardly extending recess 402a provided along the perimeter of each cover. The at least one recess can be provided with a second similar recess 402b at the opposite edge of the cover. The coordinating recesses can effectively compartmentalize wearable device 400 into modules 403a, 403b and 403c, and provide an added dimension of flexibility and conformity to the wearable device for enabling a comfortable placement of wearable device 400 on complex contours of a user's body.

The compartments or modules depicted in FIG. 8 preferably house at least one system component, such as the battery supply 118 in module 403a, flexible reservoir 106 and pump mechanism 114 in module 403b, and flexible PCB 416 in module 403c. An entire component can be positioned inside a single compartment or module. By positioning the system components within the compartments, as illustrated in FIG. 8, only a flexible connection extends from one compartment to the next. The area of greatest flexibility and conformity of wearable device 400 is where the individual compartments conjoin. Thus, by positioning the system components in the separate compartments, maximum flexibility and conformity of wearable device 400 can be realized.

FIGS. 9A and 9B illustrate a fourth exemplary embodiment of a multi-dimensionally flexible wearable device 500 that is also compartmentalized into modules or lobes and even further enhances the multi-dimensional conformity of the wearable device. The upper and lower covers, 502 and 504, of wearable device 500, can comprise a central "hub" area 503 of arbitrary shape and dimension, and a plurality of modules or lobes 505a-505d, also of arbitrary shapes, that extend radially from the central hub 503. Similar to the exemplary embodiment described in connection with FIG. 8, wearable device 500 can house at least one system component in each of the lobes 505a-505d and the central hub 503. Each lobe can entirely incorporate the system component positioned therein. Wearable device 500 is most flexible and conformal near the area where each of lobes 505a-505d conjoin the central hub area 503. Thus, the device can be configured such that only a flexible connection extends from each lobe 505a-505d to the central hub 503. In exemplary embodiments of the present invention, specific components can be arranged and shaped so as to adopt the overall or compartmental shape and mode of flexure of the upper and lower covers, such as the flexible PCB 516 shown in FIGS. 9A and 9B adopting the shape of central hub area 503, as well as flexible PCB 416 depicted in FIG. 8.

The specific components shown in FIGS. 9A-9B, as being contained within wearable device 500, are provided only by example, and are not intended to be limiting. One of ordinary skill in the art will understand that the specific components and arrangement of components within the wearable device 500 and especially within the individualized compartments will vary depending on the intended functionality of wearable device 500. Any combination of components necessary for realizing a desired functionality of wearable device 500 can be advantageously chosen and positioned within the flexible housing to achieve maximum flexibility and conformity of wearable device 500. Additionally, the shape of upper and lower covers, 502 and 504, as shown in FIGS. 9A and 9B, is not limiting of exemplary embodiments of the present invention. One of ordinary skill in the art will understand that the device can be formed into any suitable shape that is flexible and conformal to the user's body.

The embodiment illustrated in FIG. 9A provides an additional level of comfort for the user in addition to that achieved by the flexible design. As shown in FIG. 9A, lower cover 504 can be affixed to the user's skin with adhesive pads 510 provided on each of the radially extending lobes 505a-505d. Alternatively, an adhesive layer can be provided that substantially covers the entire surface area of the portion of the housing that is affixed to the user.

The skin of some users might be particularly sensitive to the adhesive that is used. The separate adhesive pads 510, as shown in FIG. 9A, reduce the total surface area of the user's skin on which the adhesive is applied, and allow the user's skin between the pads to stretch more comfortably, thus minimizing potential skin irritation and pain associated with the use of wearable device 500.

Figure 9C:
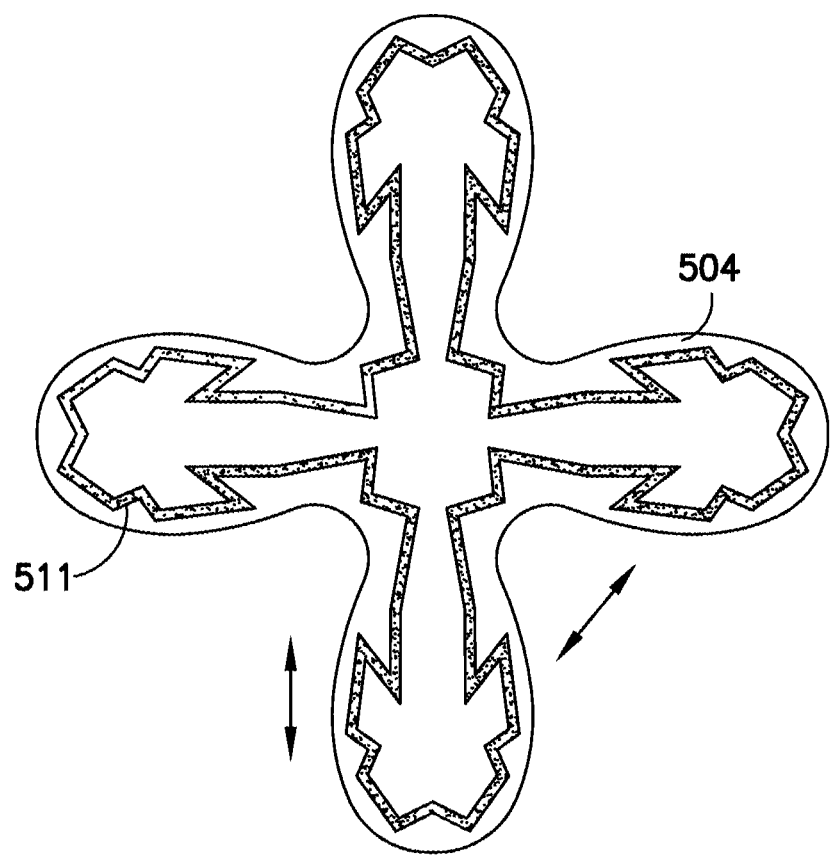
FIG. 9C is a bottom view of the assembled wearable device shown in FIG. 9B, showing an exemplary adhesive pattern layout.
Figure 9D:
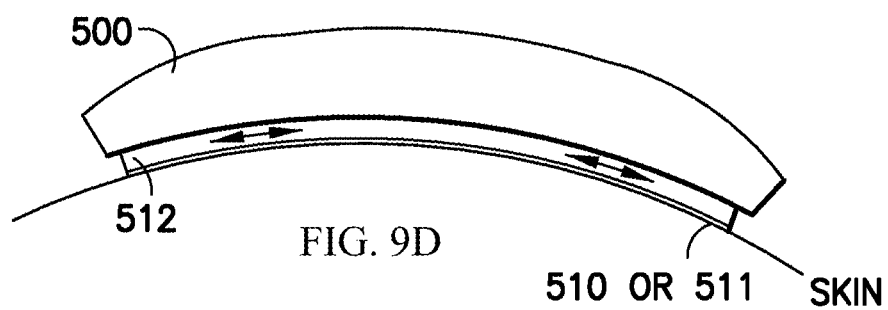
FIG. 9D is a side view of the assembled device shown in FIGS. 9B and 9C, adhered to the skin of a user.

In other embodiments, the adhesive layer for use with exemplary embodiments of a wearable device can adopt a pattern that enhances flexibility along the perimeter of the wearable device for enabling increased freedom of movement at the interface of the user's skin and the exemplary wearable device, such as a zig-zag pattern. For instance, a pattern 511 as shown in FIG. 9C for use with the wearable device shown in FIGS. 9A and 9B, can be used in exemplary embodiments. A similar pattern can be adopted for use with any shape of the above described exemplary wearable devices, as would be understood by one of ordinary skill in the art. Such a pattern reduces a user's awareness of the physical sensation accompanied by the adhesive interface and enables flexibility by allowing subtle movement to occur on the surface of the skin during normal physical activity. The adhesive layer can also be formed or formulated from a flexible material so as to enable subtle stretching of the adhesive layer, thus further enhancing comfort and flexibility of the wearable device. The freedom of movement provided by such an adhesive can be subtle and can be configured so as to not cause undesirable movement at the infusion site. Nevertheless, an additional non-flexible adhesive ring or perimeter, acting as an anchor, can be provided at the infusion site for preventing any undesirable movement at this site. Additional embodiments of the present invention can also comprise an adhesive layer of any desired shape or size with an increased thickness, or an elastomer or foam layer 512 sandwiched between the adhesive layer and the wearable device, as shown in the side profile of wearable device 500 depicted in FIG. 9D, for providing additional freedom of movement and flexibility. The thickness of layer 512 can be chosen to provide an increased overall flexibility of an exemplary wearable device without overly increasing the profile of the wearable device while affixed to the user's skin. The above embodiments are not limited to the wearable device 500 as shown but can be provided with any of the above exemplary wearable devices.

The specific components and arrangement of the components that are depicted in FIGS. 6-9 are not meant to be limiting and are provided to illustrate concepts of various embodiments of the present invention. Wearable devices according to exemplary embodiments of the present invention can incorporate any combination of the components to be discussed below, as well as any other components available in the art for realizing specific functionality of a wearable medical device. The specific components are preferably provided in any advantageous arrangement for enabling a thin, flexible, conformal wearable device, as will be understood by one of ordinary skill in the art.

Controller 116, as shown in FIG. 5, in an exemplary embodiment of the present invention, can be provided at least for controlling pump mechanism 114 or a fluid metering device. Controller 116 can comprise an ultra-low-power (ULP) programmable controller that combines the necessary processing power and peripheral set to control drug delivery through the pump mechanism 114, as well as to perform other optional system tasks, such as system or flow monitoring and communication with a host device or other external devices. Controller 116 can be embodied in an integrated circuit (IC) or a "system on a chip" (SoC) including any other circuitry, such as that necessary for communication with a host device. SoC designs can be used that consume less power and have a lower cost and higher reliability than a multi-chip system. By providing a single chip system, overall size and area of the electronic components can be reduced and the arrangement of such components can be simplified.

The IC or SoC, in an exemplary embodiment of the present invention, is preferably provided on a flexible printed circuit board (PCB) 216, 316, 416, and 516 as shown in FIGS. 6-9, respectively. Flexible PCBs are well known in the art. The flexible printed circuit boards can provide wiring and support for connecting leads of various electrical components to the controller 116 and power supply 118, such as pump mechanism 114, an automatic infusion needle mechanism 108, and an optional communication transceiver, hematocrit sensor, blood pressure sensor, blood glucose sensor, SpO2 sensor, piezoelectric pump, squiggle motor, as well as any other electronic component. The flexible PCB, in each of the exemplary embodiments, can be as flexible as the exemplary lower cover of the wearable device, so as not to inhibit the overall flexibility of the wearable device.

Power supply 118, in exemplary embodiments of the present invention, can comprise a thin flexible battery or batteries and/or supercapacitors. Flexible, thin supercapacitors and lithium-polymer batteries are well known in the art and can be used in exemplary embodiments of the present invention. Power supply 118 can comprise disposable or rechargeable power sources. One of ordinary skill in the art will appreciate that any known power supply that is thin can be suitable for providing a power supply 118 in exemplary embodiments of the present invention. The power supply can be flexible. In an alternative embodiment, a small rigid battery or batteries connected by flexible conductors can be used. The embodiments of power supply 118 illustrated in FIGS. 6 9 are not limiting and are provided merely to depict exemplary arrangements of a power supply in a wearable medical device according to exemplary embodiments of the present invention. Power supply 118, in an alternative embodiment of the present invention, can be provided using energy harvesting techniques, alone or in combination with a standard power source, such as those disclosed in previously incorporated U.S. Pat. No. 8,939,928 B2. Power supply 118 can be connected to the flexible PCB using flexible contacts. If multiple batteries are implemented, each of the batteries can be connected to each other using flexible contacts and can be spaced apart to promote optimum flexibility of wearable device 100.

Reservoir 106 in the exemplary embodiments illustrated in FIGS. 6-9, can comprise a flexible reservoir, pouch, or bladder for storing a drug or other therapeutic substance for delivery to the user. In an exemplary embodiment, reservoir 106 is provided to the user pre-filled. Reservoir 106 can be constructed from a flexible polymer that is compatible with the drug or substance to be stored therein. Various shapes and dimensions of reservoir 106 are shown in FIGS. 6-9. One of ordinary skill in the art will understand that the specific illustrations are not limiting, and the design of reservoir 106 can be altered depending on the specific embodiment of wearable device 100. Reservoir 106 can be designed to be low-profile, so as to achieve a reduced overall height/thickness of wearable device 100. Reservoir 106, in exemplary embodiments, can hold a volume of drug that is sufficient for the intended duration of use of the wearable device. In some cases, however, a large required volume of drug can be prohibitive to an exemplary thin wearable device. Alternate embodiments can include a fill port and septum provided on the upper cover for enabling a user to refill reservoir 106, such as with a prefilled or fillable syringe, so as to enable a reduced surface area of the reservoir 106. In these embodiments, reservoir 106 can be fillable by the user prior to use. The wearable device can be configured such that reservoir 106 is replaceable, for example, provided with an adhesive, adhesive periphery, as a plug, or the like. A top layer of the wearable device can be configured to peel-back and expose a reservoir for swapping-out or refilling.

Common patch pumps available in the art typically include a rigid cylindrical tube as a reservoir for containing a drug and comprise a mechanism for displacing the volume within the reservoir to provide the drug to a pumping or infusion mechanism, similar to a syringe, plunger, piston, or the like. Exemplary embodiments of the present invention can employ pumping mechanisms or fluid metering devices that are capable of drawing or expelling a fluid or drug from flexible reservoir 106. Positive or negative displacement can be used to move the contents of the reservoir.

FIG. 10 shows a patient 12 wearing a wearable device 1000 and holding a wireless user interface assembly 14 for monitoring and adjusting operation of wearable device 1000, in accordance with an exemplary embodiment of the present invention. The user interface assembly 14 typically includes apparatus for entering information (such as touchscreen or keypad). The user interface can be used for transmitting information to the user (such as an LCD display, a speaker or a vibrating alarm). Wearable device 1000 is typically small and lightweight enough to remain comfortably adhered to the patient for several days or weeks.

Figure 11:
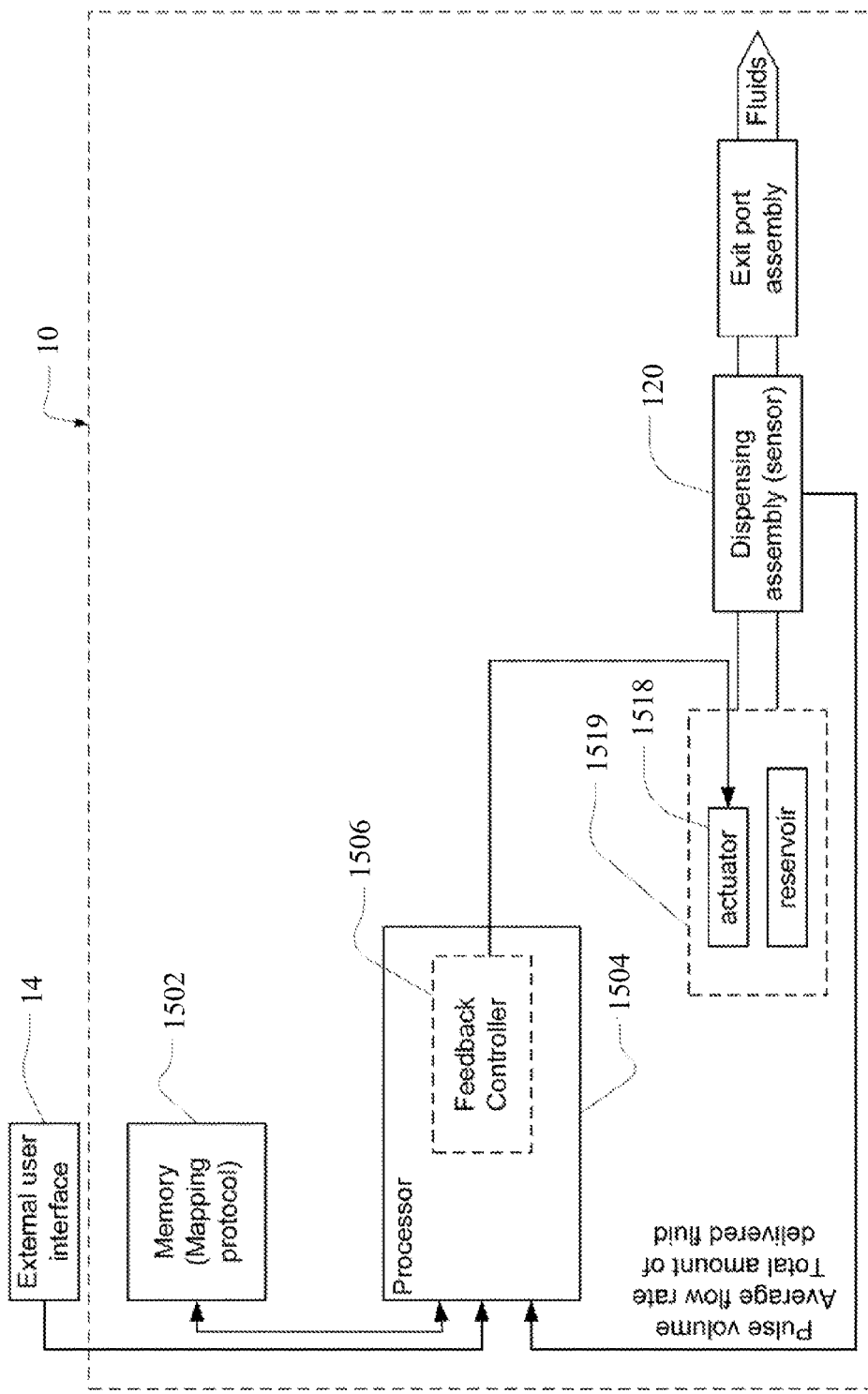
FIG. 11 is a control circuit diagram showing the components used for controlling the administering of a drug or supplement, according to various embodiments of the present invention.

FIG. 11 shows a flow diagram of a data acquisition and control scheme for an exemplary embodiment of a fluid delivery system. A patient or caregiver utilizes an external user interface 14 which is typically a base station or handheld unit housed separately from the wearable device 1000. In some embodiments, the user interface 14 is integrated with a computer, cell phone, personal digital assistance, or other consumer device such as an APPLE watch. The user interface assembly can be in continuous or intermittent data communication with wearable device 1000 via wireless radio frequency transmission (for example, via LF, RF, or standard wireless protocols such as "Bluetooth") but could also be connected via data cable, optical connection or other suitable data connection. The external user interface 14 communicates with a processor 1504 to input control parameters such as body mass, fluid dose ranges or other data and receives status and function updates such as the presence of any error conditions resulting from occluded flow, leaks, empty reservoir, poor battery condition, need for maintenance, passage of an expiration date, total amount of fluid delivered or remaining or unauthorized disposable component. The interface 14 can transmit error signals to a patient's guardian or medical professional through a telephone, email, pager, instant messaging, or other suitable communication medium. A reservoir actuator assembly 1519 includes an actuator 1518 and a reservoir 1520. The dispensing assembly 120 transmits data related to flow through the flow line to the processor 1504. The processor 1504 uses the flow data to adjust the action of the actuator 1518 in order to increase or decrease flow from the pump assembly 1519 to approximate the desired dosage and timing. Optionally, a feedback controller 1506 of the processor 1504 can receive data related to the operation of the reservoir pump assembly 1519 for detection of conditions such as open or short circuit faults, or actuator temperature.

In another aspect of the present invention, the wearable pump patch can include heart rate, blood pressure, and blood-oxygen sensors. Alternatively, or in addition to the wearable pump patch, a separate patch can be applied to a patient's body that includes any of a heart rate sensor, a blood pressure sensor, and a blood-oxygen sensor. An example of a wearable patch having these sensors can be found in U.S. Patent Application Publication No. US 2019/0254541 A1, which is incorporated herein in its entirety by reference.

The wearable device and sensing system can be configured to record pulse pressure waves by photoplethysmography. Blood volume changes in peripheral arteries are detected by optical sensors based on principles of light scattering. Such optical sensors can be placed on the chest, wrist, or finger of a subject. Non-invasive arterial pressure measurements can be measured by the sphygmomanometer, which includes inflatable cuffs commonly used in doctor's offices, clinics, and in home-based settings.

In some embodiments of the invention, semiconductor strain gauge sensors are included in patch systems that can be applied to the skin of a subject. In some embodiments of the invention, semiconductor strain gauge sensors are included in electrodes. Semiconductor strain gauge materials can be used to measure transit time and wave form of a blood pressure wave by placing sensors including semiconductor strain gauge materials on or near blood vessels, such as externally near an artery, such as on the neck, wrist, or temple, internally on or near an artery, or combinations of such placements. Sensors including semiconductor strain gauge materials can be used to determine blood pressure.

Embodiments of the invention can provide reliable, non-invasive measurements of vessel expansions induced by pressure pulse waves to provide blood pressure monitoring and subject health. The time interval needed by a pulse wave to travel from the heart to a peripheral artery or from a proximal artery to a distal one, referred to as pulse transit time (PTT), can provide information pertinent to monitoring subject health. Pressure pulse waves are generated as heart contractions cause blood to travel to peripheral arteries. A pulse pressure wave contains information relevant to a number of internal systems and processes. Pulse wave velocity depends, in part, on arterial pressure.

Systolic and diastolic arterial pressure can be estimated from PTT. PTT can be obtained by using two sensors that record electrocardiogram (ECG) and a plethysmogram, or two plethysmograms taken at different locations by either piezoelectric or piezoresistive sensors. Arterial pressure can be determined from PTT through the Moens-Korteweg equation, taking into account constitutive laws for arterial stiffness. Arterial pressure can, in some cases, be related to PTT by linear regression or non-linear formulas fit to experimental distributions of PTT-Pa data. Embodiments of the invention can measure blood flow characteristics through placement of strain gauge sensors using, for instance, Moens-Korteweg equation.

Figure 12:
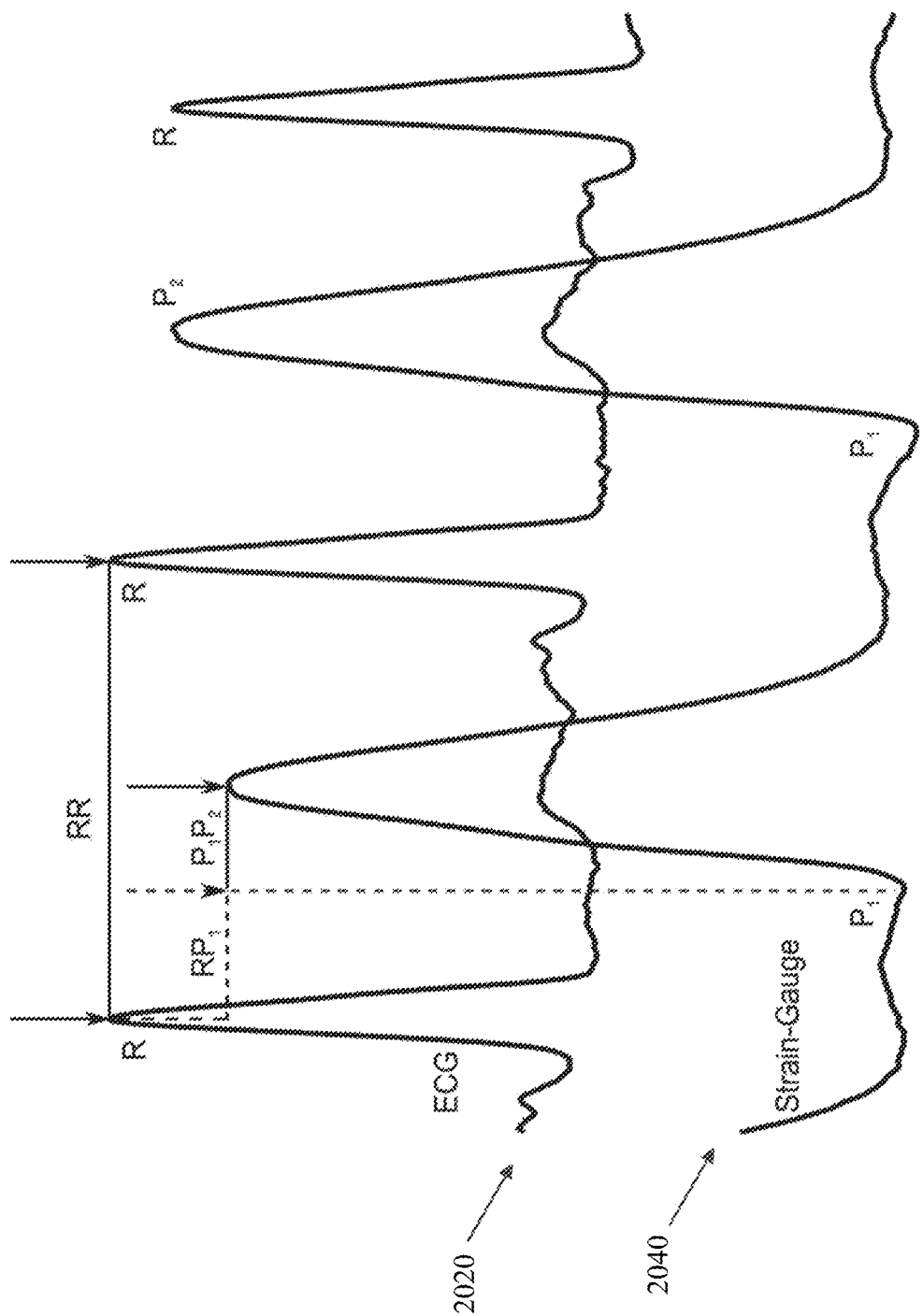
FIG. 12 depicts exemplary pressure pulse wave charts that can be used in an administering method according to the present invention.

According to aspects of the present invention, FIG. 12 depicts exemplary pressure pulse wave charts. The chart depicts a typical ECG waveform 2020. Methods and apparatuses for obtaining such signals are known. ECG signals can be, for example, digitized and analyzed according to various known methods to characterize a number of systemic features and conditions, such as heart rate and arrhythmias. The chart also depicts a strain gauge-based wave form 2040 that can be obtained according to embodiments of the invention. As shown, R represents an R peak, which can play an important role, for instance, in diagnosing heart rhythm abnormalities. According to embodiments of the invention, PTT can be obtained by using two sensors that record ECG and a plethysmogram. PTT is defined here as the time interval between the R-peak of the ECG, as shown, and the arrival of the pulse wave to one of the peripheral arteries (such as a radial artery), which can be observed via a strain gauge sensor according to embodiments of the invention as illustrated as point P1 in FIG. 12. Information attained can be used to prescribe a drug or dosage, automatically adjust a dosage for administering a drug, or both.

Systems according to embodiments of the invention can record pressure pulse waves at multiple peripheral locations, such as two or more locations, to characterize biological systems and conditions, including for instance characterization and determination of heart rate variability and systolic blood pressure. Sensors according to embodiments of the invention, including semiconductor or metal strain gauge sensors that use piezoresistive effect and/or piezoelectric-based strain gauge sensors and electrodes, can be used to record pulse transit time and the wave form of a blood pressure wave. Features of blood pressure wave form and ECG can be used, in some embodiments of the invention, for continuous estimation of systolic and diastolic arterial pressure.

Embodiments of the invention include sensors positioned on or near an artery. In some embodiments of the invention, biosensors, including strain gauge sensors, are placed on the skin at a location where an artery is capable of being compressed near the surface of the body, including at the carotid artery, brachial artery, radial artery, femoral artery, popliteal artery, posterior tibial artery, and/or the dorsalis pedis artery. In some embodiments of the invention, biosensors, including piezoresistive type strain gauge sensors and/or piezoelectric type strain gauge sensors, are implanted near an artery. For instance, biosensors can be inserted subcutaneously or can be placed directly on an artery. In some embodiments of the invention, biosensors are coated with a biocompatible material prior to insertion or implantation.

Figure 13A:
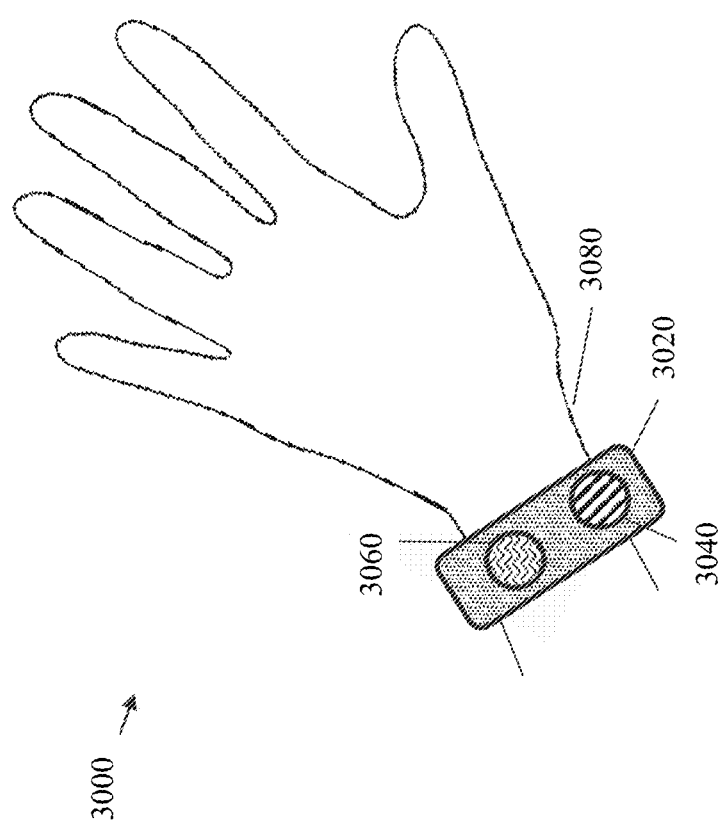
FIG. 13A depicts a wearable device useful in a system according to various embodiments of the present invention.

FIG. 13A depicts a side view of an exemplary biological monitoring system 3000 according to embodiments of the invention. As is shown, aspects of a sensing system 3000 can be applied to the surface of the skin at an area in close proximity to an artery, such the surface of the skin 3080 at a wrist. The system 3000 can include a piezoelectric or piezoresistive sensor unit 3060 and a circuitry module 3040. The piezoelectric or piezoresistive sensor unit can be a wearable sensor capable of detecting a pressure pulse wave through the skin of a subject. The circuitry module 3040 can include, for example, a microcontroller, an amplifier, an analog to digital (A/D) converter, and a power and/or data communication unit capable of communicating wirelessly or via a wired connection to an external device such as smart phone, watch, tablet, notebook, etc. In some embodiments of the invention, the piezoelectric or piezoresistive sensor unit 3060 and the circuitry module 3040 are fastened to a band or belt 3020 capable of encircling a body part, such as a wrist. The piezoelectric or piezoresistive sensor unit 3060 is positioned, in some embodiments of the invention, against the surface of the skin. The circuitry module 3040 can include a power source and can receive signals from the strain gauge sensor 3060 and the external device, such as smart phone, watch, tablet, computer, or other electronic device.

Figure 13B:
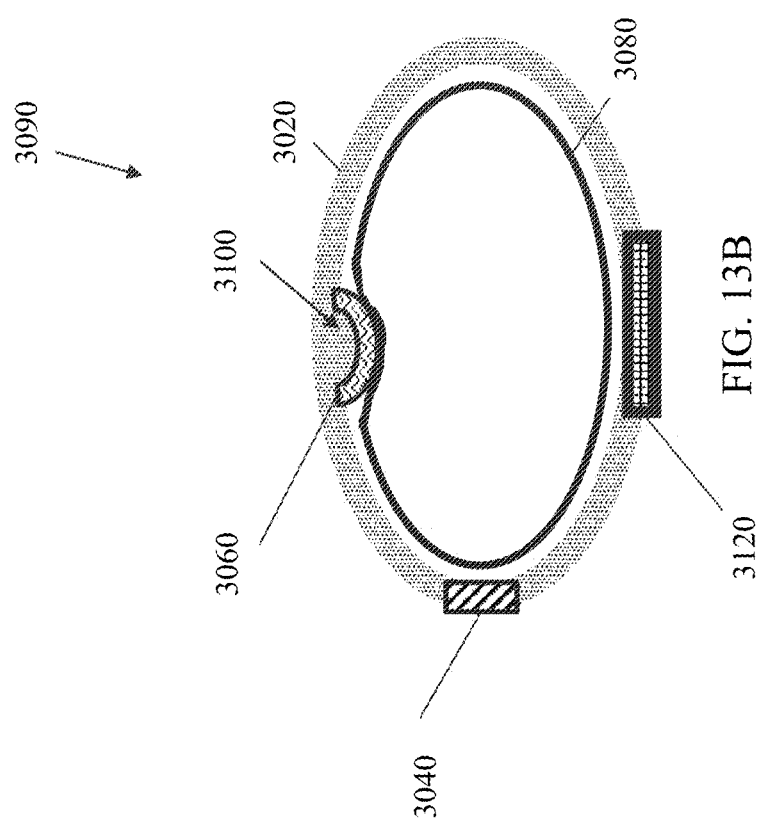
FIG. 13B depicts an end view of the wearable device shown in FIG. 13A, on the user's wrist.

FIG. 13B depicts a top down view of another exemplary biological monitoring system 3090. The system 3090 includes a piezoelectric or piezoresistive sensor unit 3060, a circuitry module 3040 electrically connected to the sensor unit 3060, and a band or belt 3020. The band or belt 3020, as shown, includes a protrusion 3100 at the location of the sensor unit 3060 to improve or enhance contact between the sensor unit 3060 and the surface of the skin 3080. In some embodiments of the invention, the band or belt 3020 includes a clasp 3120 to fasten the band or belt 3020 around the body.

Piezoelectric or piezoresistive sensor unit 306 can include piezoresistive based strain gauge sensors or piezoelectric based strain gauge sensors. In some embodiments of the invention, systems include biosensors including piezoelectric materials. In some embodiments of the invention, systems include semiconductor-based strain gauge sensors and piezoelectric based strain gauge sensors. As will be appreciated by those skilled in the art, the electrical properties of a semiconductor material in a semiconductor-based strain gauge can be adjusted by modifying dopants and/or doping conditions, such as patterns and concentrations of dopant, depending on the desired properties and applications.

Embodiments of the invention include sensors including semiconductor and/or metal (e.g. nanoparticle based) strain gauge materials. Strain gauges measure strain that can be imparted by stress, torque, and a host of other stimuli such as displacement, acceleration, and position. The gauge factor for semiconductors can be several magnitudes larger than the gauge factor for metal. Thus, the change in conductivity due to strain can be much larger in semiconductor strain gauge materials relative to conductive strain gauge materials, providing highly sensitive strain detection and measurements.

Embodiments of the invention include metal-based strain gauge sensors including, for example, nanoparticle-based materials, carbon nanotube-based materials, nanofiber-based materials, and/or combinations thereof.

In a semiconductor strain gauge material, a semiconductor substrate can provide a means of straining a silicon chip. Semiconductor base materials can be doped, for example by diffusion of doping materials, to obtain a desired base resistance. Advantageously, strain gauge materials can be several magnitudes smaller than metal sensors due in part on the difference in gauge factor. Strain gauges can be described, in some instances, with a function as follows:

$$\frac{\Delta R}{R} = \frac{\Delta \rho}{\rho} + \frac{\Delta L}{L} - \frac{\Delta A}{A}$$

where ρ is the resistivity of the material, L is the length of the material, A is the cross-sectional area of the material.

Methods of manufacturing strain gauge sensors, including semiconductor strain gauge sensors, are known. In some embodiments of the invention, a semiconductor base material of a semiconductor-based strain gauge sensor can be doped. Doping can be selective doping, such that a specific area or region of the substrate is doped, or doping can be non-selective, for example such that the entire silicon substrate is doped to obtain a base resistance as needed. Non-limiting examples of suitable dopant materials include p-type dopants (e.g., boron), n-type dopants (e.g., phosphorus, arsenide, antimony), or any combination thereof. A substrate can provide strain for a silicon chip. In some embodiments, metal connections can be provided at the ends of a device.

Piezoelectric materials that can be used include, for instance, perovskite-based materials and non-perovskite piezo-electric materials. Piezoelectric materials can include, for example, lead zirconate titanates (PZTs), potassium niobate, sodium tungstate, barium titanate (BaTiO3), and lead titanate (PbTiO3). Piezoelectric materials that directly generate a voltage that is a function of the strain can advantageously have higher efficiency than piezoresistive materials and can require less surface area. Moreover, piezoelectric based strain gauge sensors can be integrated in back end of the line (BEOL) of semiconductor manufacturing process.

Selected exemplary properties of piezoelectric materials and piezoresistive materials (semiconductor-based strain gauge materials) are depicted below. The properties of piezoelectric materials can be varied, for instance depending on materials used, based upon the desired properties and applications.

| Material | Strain sensitivity (V/με) | Threshold (με) | Span to threshold ratio |
|---|---|---|---|
| Piezoelectric | 5.0 | 0.00001 | 100,000,000 |
| Piezoresistive | 0.0001 | 0.0001 | 2,500,000 |

Figure 14A:
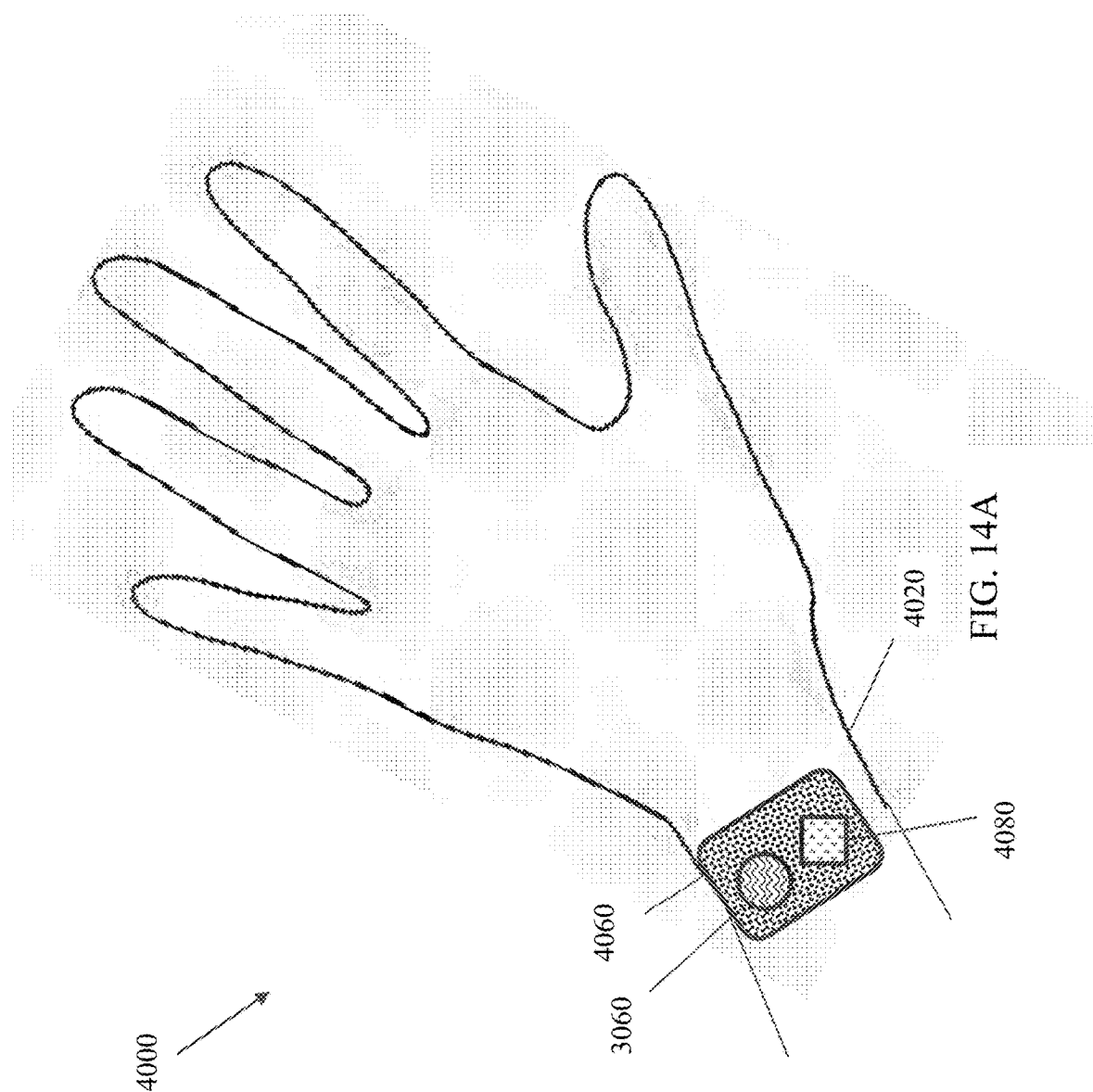
FIG. 14A depicts yet another device that can be used with or be part of the wearable device and system of the present invention.
Figure 14B:
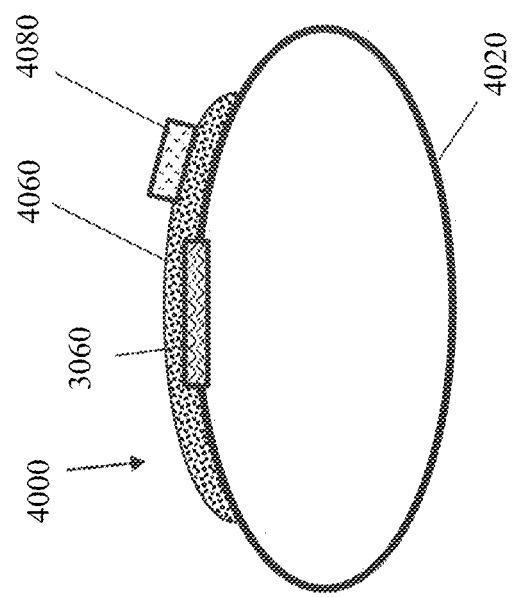
FIG. 14B is a side view of the device shown in FIG. 14A.

FIGS. 14A and 14B depict another exemplary system 4000 according to one or more embodiments of the invention, in which FIG. 14A depicts a side view of a system 4000 according to an exemplary embodiment of the invention applied to the surface of the skin at an area in close proximity to an artery, such the surface of the skin at a wrist 4020. FIG. 14B shows a top down view of the system 4000. The system 4000 can include a piezoelectric or piezoresistive sensor unit 3060, an adhesive patch 4060, and a circuitry module 4080, including control and communication circuitry for the strain gauge sensor. The strain gauge sensor can include a piezoresistive material (e.g. semiconductor) or a piezoelectric material. The adhesive patch 4060 can facilitate placement of the piezoelectric or piezoresistive sensor unit 3060 in contact with the skin. The adhesive patch can include, for instance, a backing material such as a fabric or a flexible polymer, and an adhesive material capable of maintaining the placement of a sensor against the skin, including known dermal adhesives. The piezoelectric or piezoresistive sensor unit 3060 can send signals via the circuitry module 4080 to an external device, such as a computer, tablet, or smart device.

Figure 15:
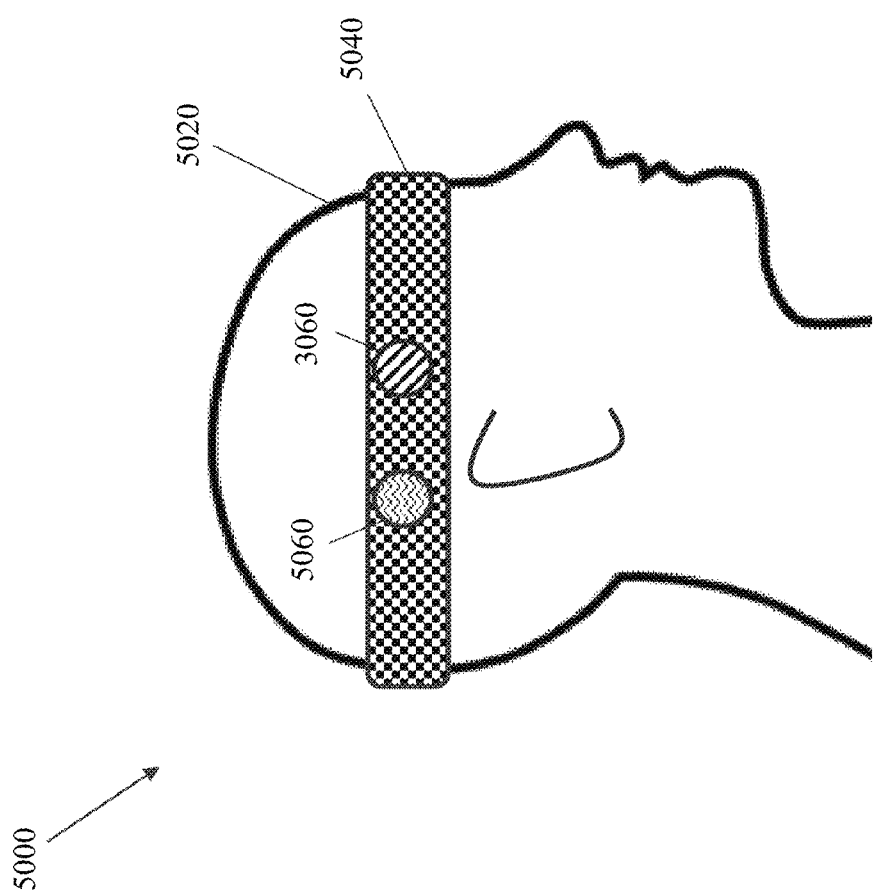
FIG. 15 depicts yet another device that can be used with or be part of the wearable device and system of the present invention.

FIG. 15 depicts another exemplary system 5000 according to one or embodiments of the invention. The system 5000 includes a headband 5040 including a piezoelectric or piezoresistive sensor unit 3060 and a circuitry module 5060. The headband 5040 can be placed around a user's head 5020 so as to position the sensor 3060 near the temporal artery. The circuitry module 5060, which can include communication circuitry, can be placed on the headband, as shown.

Figure 16B:
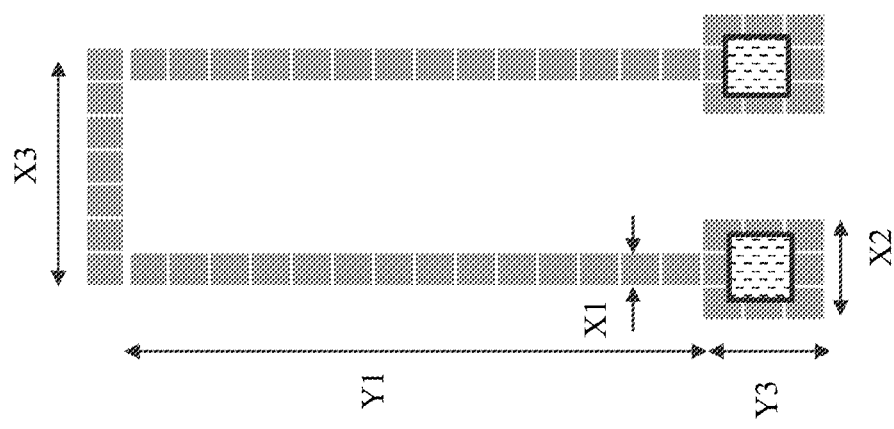
FIGS. 16A-16D depict various strain gauge linear patterns that can be used with and in strain gauges of devices and systems according to the present invention.
Figure 16A:
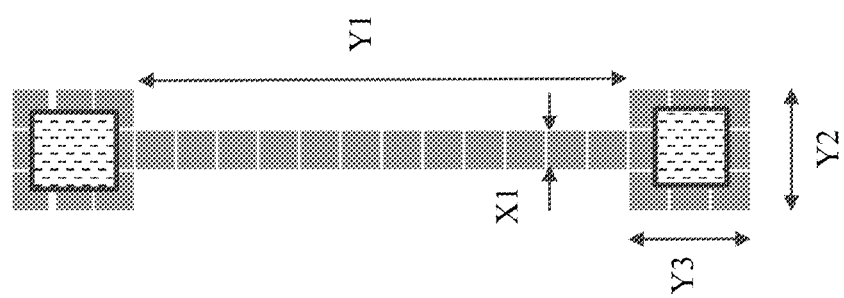
Figure 16D:
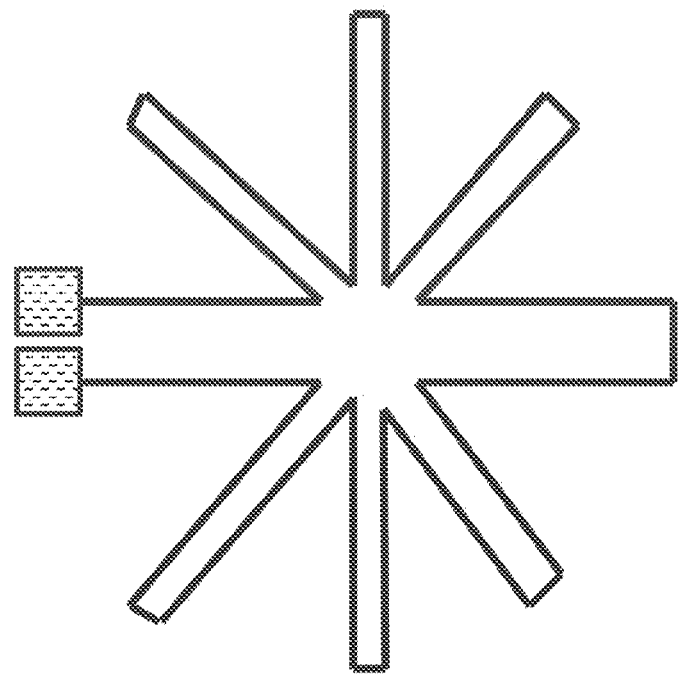
Figure 16C:
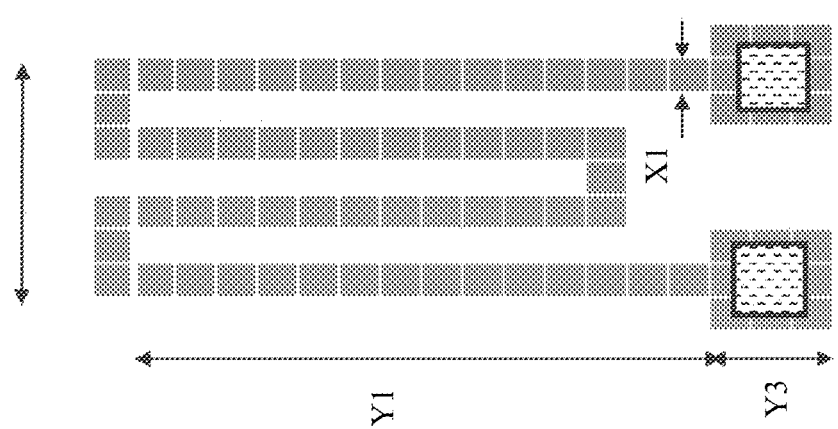
Figure 17:
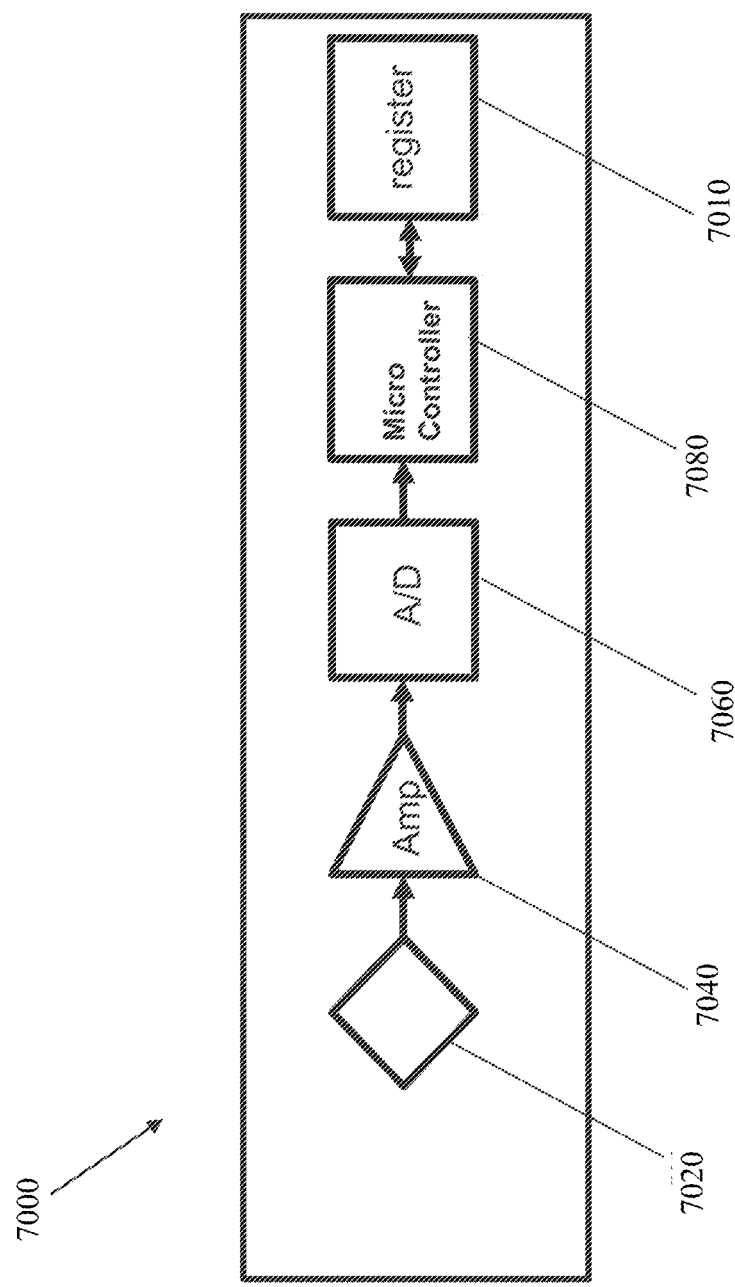
FIG. 17 is a schematic diagram of a strain gauge monitor that can be used with or as part of the device and system of the present invention.
Figure 18:
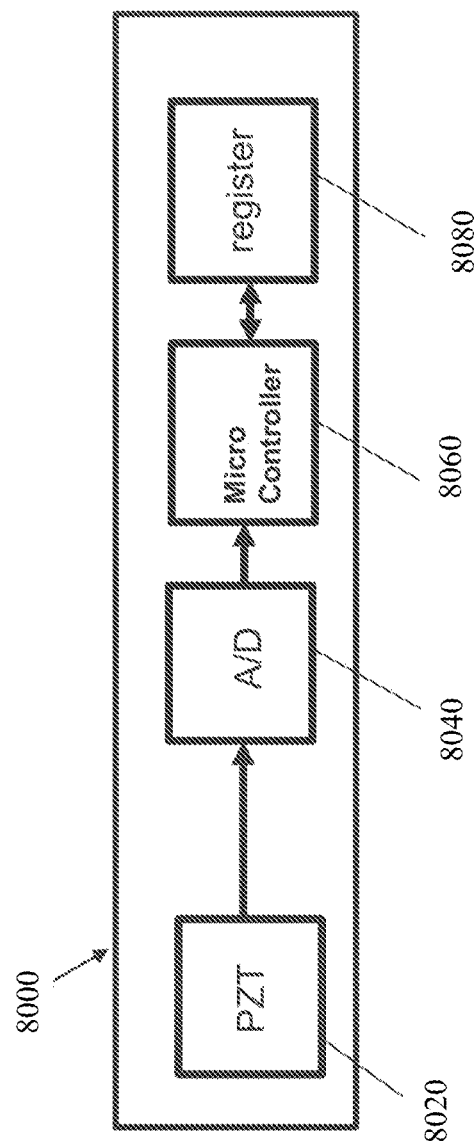
FIG. 18 is schematic diagram of a strain gauge monitor that can be used with or as part of the device and system of the present invention.

Strain gauge sensor units according to embodiments of the invention, for instance systems as depicted in FIGS. 17 and 18, can be placed at single or multiple locations on a body. Embodiments of the invention including multiple strain gauge sensors can be formed in a variety of patterns and configurations. FIGS. 16A-16D depict shape of piezoresistive type strain gauge sensors according to embodiments of the invention.

FIG. 16A depicts a linear pattern in which two strain gauge sensing pads are in a linear configuration separated by a connecting line of distance Y1 from 50 μm to 50 mm, and having a width X1 from 2 μm to 10 mm. The sensing pads can each have a width X2 from 50 μm to 5 mm and height Y3 from 50 μm to 5 mm. FIG. 16B depicts a u-shaped pattern in which two sensing pads, in which the connecting line X3 can have a length, for instance of 6 μm to 30 mm. FIG. 16C and FIG. 16D depict alternate configurations including connecting lines including a plurality of deflection points.

FIG. 17 depicts a schematic of an exemplary strain gauge sensor unit 7000 according to embodiments of the invention. The strain gauge sensor unit 7000 includes a semiconductor-based strain gauge sensor including a Wheatstone bridge circuit 7020. A Wheatstone bridge circuit 7020 consists of resistors and it has the ability to provide accurate measurements. The unit 7000 also includes an amplifier circuit 7040 used for increasing amplitude of output signal from the Wheatstone bridge circuit 7020 and an analog to digital (A/D) converter 7060. The strain gauge sensor unit 7000 can also include a microcontroller 7080. The microcontroller 7080 receives signals from A/D converter 7060 and can have a capability of signal processing. In some embodiments of the invention, signal processing is performed by one or more external devices in communication with the exemplary strain gauge sensor unit 7000. The strain gauge sensor unit 7000 can also include a register 7100 including, for instance, flash memory and/or SRAM.

FIG. 18 depicts a schematic of another exemplary strain gauge sensor unit 8000 according to embodiments of the invention. The strain gauge sensor unit 8000 includes a piezoelectric strain gauge sensor 8020. The unit 8000 also includes an analog to digital (A/D) converter 8040 that converts the analog signals coming from the piezoelectric strain sensor 802 into digital signals for input into microcontroller 8060. The strain gauge sensor unit 8000 can also include a microcontroller 8060. The microcontroller 8060 receives signals from A/D Converter 8040 and can have signal processing capabilities. The strain gauge sensor unit 8000 can also include a register 8080.

Advantageously, PZT sensors can be self-powered, for instance directly generating voltage that is a function of strain. In some embodiments of the invention, a piezoelectric strain gauge sensor unit does not have an external power system.

Figure 19:
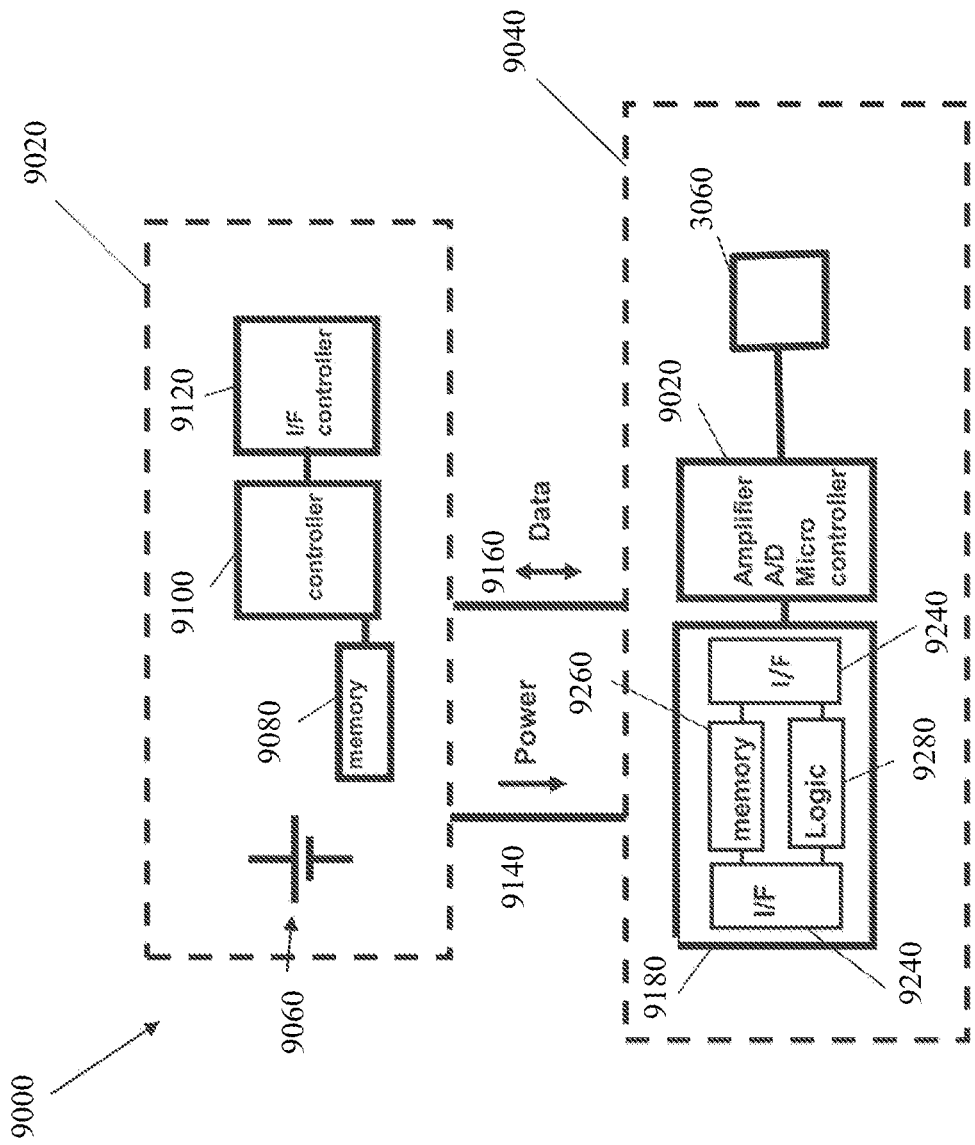
FIG. 19 is a schematic diagram of a strain gauge monitor that can be used with or as part of the device and system of the present invention.

FIG. 19 depicts a schematic of an exemplary strain gauge sensor system 9000 according to one or more embodiments of the invention. The system 9000 includes a sensing patch or band 9040 and an external computing device 9020 electrically and mechanically connected by wires. The sensing patch or band 9040 can include a strain gauge sensor integrated within an adhesive patch, wrist band, head band, leg band, or other patch or band suitable for positioning a strain gauge sensor at or near an artery.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such a range is separately disclosed. Where a range of numerical values is recited herein, unless otherwise stated, the range is intended to include the endpoints thereof, and all integers and fractions within the range. It is not intended that the scope of the invention be limited to the specific values recited when defining a range.

All patents, patent applications, and publications mentioned herein are incorporated herein in their entireties, by reference, unless indicated otherwise.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A wearable device, the device comprising:
   a housing configured to be attached to the skin of a patient during use;
   a first drug reservoir within the housing, containing an amount of a first drug;
   a second drug reservoir within the housing, containing an amount of a second drug, the first drug and the second drug being interdependent on one another;
   an injector assembly at least partially housed in the housing and configured to inject (1) a first drug into the patient, through the patient's skin, and (2) the second drug into the patient, through the patient's skin, the first drug reservoir being in fluid communication with the injector assembly, and the second drug reservoir being in fluid communication with the injector assembly;
   a first sensing system configured to sense one or more patient parameters that are indicative of a need to administer the first drug to the patient, the first sensing system comprising one or more sensors and a control signal generator, the control signal generator being configured to generate a control signal in response to the one or more patient parameters that are sensed;
   a second sensing system configured to sense one or more patient parameters that are indicative of a need to administer the second drug to the patient, the second sensing system comprising one or more second sensors and a second control signal generator, the second control signal generator being configured to generate a second control signal in response to the one or more patient parameters that are sensed by the second sensing system;
   a control system within the housing and configured to receive control signals from the first sensing system and from the second sensing system, and, based on the control signals received, activate the injector assembly to (i) inject the first drug into the patient, (ii) inject the second drug into the patient, or (iii) inject both the first drug and the second drug into the patient;

a first drug level sensor configured to sense the amount of the first drug in the first drug reservoir and to generate a first drug supply signal;

a second drug level sensor configured to sense the amount of the second drug in the second drug reservoir and to generate a second drug supply signal; and a transmitter, in the wearable device, configured to transmit the first drug supply signal and the second drug supply signal to a remote device.

2. The wearable device of claim 1, wherein the first drug is erythropoietin and the second drug is an iron supplement.

3. The wearable device of claim 1, wherein the first drug is selected from epoetin alfa, epoetin beta, and darbepoetin alfa.

4. The wearable device of claim 1, wherein the control system is configured to receive an input signal from a remote device, the input signal comprising a set of instructions for the control system to carry out, the set of instructions comprising a timing instruction and an amount instruction to be used by the control system, along with the control signal received from the first sensing system, to activate the injector assembly and control (a) the timing and amount of injection of the first drug into the patient, and (b) the timing and amount of injection of the second drug into the patient.

5. The wearable device of claim 1, and a remote device, the remote device comprising a sensor configured to sense a patient parameter, and a signal generator configured to generate a remote control signal indicative of the sensed patient parameter, wherein the control system is configured to receive the remote control signal from the remote device, and, based on the received remote control signal and the control signal received from the first sensing system, activate the injector assembly and control (a) the timing and amount of injection of the first drug into the patient, and (b) the timing and amount of injection of the second drug into the patient.

6. The wearable device of claim 1, wherein the first sensing system comprises:
a pulse oximeter;
a hematocrit sensor;
a hemoglobin sensor; and
a blood pressure sensor.

7. The wearable device of claim 1, wherein the injector assembly comprises a single injector device configured to inject the first drug and the second drug simultaneously, alternately, or intermittently, into the patient through the patient's skin.

8. The wearable device of claim 1, further comprising a drug delivery system comprising a pump, wherein the pump is configured to pump the first drug, the second drug, or both, through the injector assembly and into the patient, through the patient's skin.

9. The wearable device of claim 1, wherein the wearable device is configured for the management of anemia, the first drug comprises erythropoietin, the control system comprises a microprocessor and a memory, the memory has stored therein a plurality of hemoglobin values and a plurality of respective change values each corresponding to a required change in erythropoietin administration rate based on the determined hemoglobin value, and the control system is configured to:
determine a level of hemoglobin in a patient to which the wearable device is attached;
compare the level of hemoglobin determined to hemoglobin values stored in the memory; and
regulate a rate of injection of erythropoietin by changing the rate of injection of erythropoietin by a value corresponding to the required change value stored in the memory and corresponding to the hemoglobin value determined.

10. The wearable device of claim 1, wherein the injector assembly comprises a first injector device and a second injector device, the second drug is an iron supplement, and the second injector device comprises an iontophoretic transdermal iron delivery patch.

11. The wearable device of claim 1, wherein the transmitter is configured to wirelessly transmit the first drug supply signal and the second drug supply signal to the remote device.

12. A network of devices that communicate with one another, the devices comprising the wearable device of claim 1, a physician computer processor, and a pharmacy computer processor, wherein the transmitter of the wearable device is further configured to wirelessly transmit drug information pertaining to the amount and expiration date of the first and/or second drug contained in the wearable device, the physician computer processor comprises a receiver for receiving the drug information and a transmitter for transmitting prescription information that is based on the drug information, and the pharmacy computer processor comprises a receiver for receiving the prescription information.

13. A method of maintaining a prescribed drug in the wearable device of the network of claim 12, the method comprising:
transmitting drug information from the transmitter of the wearable device to the physician computer processor, wherein at least some of the transmitting occurs wirelessly and the transmitting comprises directly transmitting or indirectly transmitting through one or more intermediate devices;
receiving, at the physician computer processor, the transmitted drug information;
transmitting a prescription from the transmitter of the physician computer processor to the pharmacy computer processor, the prescription being for the first drug, the first drug being a drug for the treatment of anemia, the prescription being based, at least in part, on the drug information transmitted;
receiving, at the pharmacy computer processor, the transmitted prescription; and
preparing a reservoir of the first drug, the reservoir being configured to be inserted into and connected to the wearable device.

14. A network of devices that communicate with one another, the devices comprising the wearable device of claim 1 and a physician computer processor, wherein the wearable device further comprises a memory, the control system is configured to store in the memory injection history information pertaining to the amount of the first drug injected and the time of the injection, for injections made by the wearable device, the transmitter is configured to wirelessly transmit the injection history information, and the physician computer processor comprises a receiver for receiving the injection history information.

15. A method of reporting information pertaining to use of the wearable device of the network of claim 14, the method comprising:
transmitting injection history information from the transmitter of the wearable device to the physician computer processor, wherein at least some of the transmitting occurs wirelessly and the transmitting comprises directly transmitting or indirectly transmitting through one or more intermediate devices;

receiving, at the physician computer processor, the transmitted injection history information;
comparing the injection history information to one or more patient parameters sensed by the first sensing system; and
transmitting operating instructions to the control system for the control system to use in operating the wearable device.

16. The wearable device of claim 1, further comprising an adhesive layer, the adhesive layer having one side attached to a bottom surface of the housing, an opposite side configured to adhere the housing to the skin of a patient, and a hole formed therein, the hole being aligned with the injector assembly so that the injector assembly can inject the first drug, the second drug, or both, into the patient's skin without needing to penetrate the adhesive layer.

17. The wearable device of claim 1, wherein the injector assembly comprises a retractable hypodermic needle configured to extend out of the housing, penetrate into the patient's skin, and retract into the housing.

18. A wearable device comprising:
a housing configured to be attached to the skin of a patient during use;
an injector assembly at least partially housed in the housing and configured to inject (1) a first drug into the patient, through the patient's skin, and (2) a second drug into the patient, through the patient's skin;
a first sensing system configured to sense one or more patient parameters that are indicative of a need to administer the first drug to the patient, the first sensing system comprising one or more sensors and a control signal generator, the control signal generator being configured to generate a control signal in response to the one or more patient parameters that are sensed; and
a control system within the housing and configured to receive a control signal from the first sensing system and, based on a control signal received, activate the injector assembly to inject the first drug into the patient, wherein
the wearable device is configured for the management of anemia, the first drug comprises erythropoietin, the control system comprises a microprocessor and a memory, the first sensing system comprises a pulse oximeter, a hemoglobin sensor, and a blood pressure sensor, the memory has stored therein a three-dimensional matrix of evaluation triplets and assigns to each evaluation triplet a value corresponding to a required change in a rate of injection of erythropoietin, and the control system is configured to:
(1) calculate a first evaluation quantity ($O_2$ Sat) based on an amount of blood oxygen sensed by the pulse oximeter;
(2) calculate a second evaluation quantity (Hemo) based on a level of hemoglobin sensed by the hemoglobin sensor;
(3) calculate a third evaluation quantity (BP) based on a blood pressure sensed by the blood pressure sensor;
(4) form an evaluation triplet ($O_2$ Sat/Hemo/BP) from the first evaluation quantity, the second evaluation quantity, and the third evaluation quantity; and
(5) compare the evaluation triplet to evaluation triplets stored in the memory; and
(6) regulate a rate of injection of erythropoietin by changing the rate of injection of erythropoietin by a value corresponding to the required change value stored in the memory and corresponding to the evaluation triplet formed.

19. The wearable device of claim 18, and a physician network computer, wherein the wearable device further comprises a transmitter configured to transmit the first evaluation quantity, the second evaluation quantity, and the third evaluation quantity, to the physician network computer.

* * * * *